(12) United States Patent
Miller

(10) Patent No.: US 7,569,823 B2
(45) Date of Patent: *Aug. 4, 2009

(54) COMPACT NEAR-IR AND MID-IR CAVITY RING DOWN SPECTROSCOPY DEVICE

(75) Inventor: J. Houston Miller, Barnesville, MD (US)

(73) Assignee: The George Washington University, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/674,573

(22) Filed: Feb. 13, 2007

(65) Prior Publication Data

US 2008/0111993 A1    May 15, 2008

Related U.S. Application Data

(63) Continuation-in-part of application No. 11/558,445, filed on Nov. 10, 2006, now Pat. No. 7,541,586.

(60) Provisional application No. 60/866,181, filed on Nov. 16, 2006.

(51) Int. Cl.
G01J 5/02 (2006.01)
(52) U.S. Cl. .................. 250/343; 250/339.07
(58) Field of Classification Search ............... 250/343, 250/370.09; 356/432, 437, 439
See application file for complete search history.

(56) References Cited

U.S. PATENT DOCUMENTS

| 5,528,040 A | 6/1996 | Lehmann |
| 5,815,277 A | 9/1998 | Zare |
| 5,903,358 A | 5/1999 | Zare |
| 5,912,740 A | 6/1999 | Zare |
| 6,084,682 A * | 7/2000 | Zare et al. ............. 356/437 |
| 6,084,687 A | 7/2000 | Miyazaki |
| 6,392,753 B1 * | 5/2002 | Logunov ............. 356/519 |
| 6,466,322 B1 | 10/2002 | Paldus |

(Continued)

FOREIGN PATENT DOCUMENTS

WO    WO 99/20996    4/1999

(Continued)

OTHER PUBLICATIONS

Muller et al., "A continuous-wave optical parametric oscillator for mid infrared photoacoustic trace gas detection", [online], Oct. 2004 [retrieved on Feb. 13, 2008]. Retrieved from the Internet:<URL:http://www.exphy.uni-duesseldorf.de/Publikationen/Papers/tops47158_03.pdf>.*

(Continued)

*Primary Examiner*—David P Porta
*Assistant Examiner*—Yara B Green
(74) *Attorney, Agent, or Firm*—Todd Juneau

(57) ABSTRACT

This invention relates to a compact cavity ring down spectrometer for detection and measurement of trace species in a sample gas using a tunable solid-state continuous-wave mid-infrared PPLN OPO laser or a tunable low-power solid-state continuous wave near-infrared diode laser with an algorithm for reducing the periodic noise in the voltage decay signal which subjects the data to cluster analysis or by averaging of the interquartile range of the data.

4 Claims, 18 Drawing Sheets

Experimental Setup

U.S. PATENT DOCUMENTS

| | | | |
|---|---|---|---|
| 6,504,145 B1 | 1/2003 | Romanini | |
| 6,532,071 B2 | 3/2003 | Zare | |
| 6,654,392 B1 * | 11/2003 | Arbore et al. | 372/20 |
| 6,694,067 B1 | 2/2004 | OKeefe | |
| 6,727,492 B1 | 4/2004 | Ye | |
| 6,787,776 B2 | 9/2004 | Webber | |
| 6,795,190 B1 | 9/2004 | Paul | |
| 7,154,595 B2 | 12/2006 | Paldus | |
| 7,277,177 B2 * | 10/2007 | Augustine et al. | 356/437 |
| 2003/0189711 A1 * | 10/2003 | Orr et al. | 356/484 |
| 2003/0210398 A1 | 11/2003 | Augustine | |
| 2005/0134836 A1 * | 6/2005 | Paldus et al. | 356/73 |
| 2006/0119851 A1 * | 6/2006 | Bounaix | 356/437 |

FOREIGN PATENT DOCUMENTS

| | | |
|---|---|---|
| WO | WO 00/65300 | 11/2000 |
| WO | WO 01/53785 | 7/2001 |
| WO | WO 03/050489 | 6/2003 |
| WO | WO 03/098173 | 11/2003 |
| WO | WO 2004/053479 | 6/2004 |
| WO | WO 2004/068123 | 8/2004 |
| WO | WO 2005/024399 | 3/2005 |
| WO | WO 2005/038423 | 4/2005 |
| WO | WO 2005/038436 | 4/2005 |
| WO | WO 2005/057147 | 6/2005 |
| WO | WO 2005/057189 | 6/2005 |
| WO | WO 2005/088274 | 9/2005 |
| WO | WO 2005/088277 | 9/2005 |
| WO | WO 2005/088278 | 9/2005 |
| WO | WO 2006/054117 | 5/2006 |

OTHER PUBLICATIONS

Awtry et al., "Development of cw-laser based cavity-ringdown sensor aboard a spacecraft for trace air constituents", Applied Physics B: Laser and Optics; vol. B 75; pp. 255-260; Aug. 21, 2002.*

MTO-1000-H2O-Trace Moisture Analyzer for Inert, Passive, Toxic, and Corrosive Gases; Aug. 7, 2003; [retrieved on Feb. 13, 2008]; Retrieved from the Internet:<URL:http://www.tigeroptics.com/pdf/MTO_1000_H2O.pdf.>.*

Fawcett et al., "Trace detection of methane using continuous wave cavity ring-down spectroscopy at 1.65 microns"; Physical Chemistry Chemical Physics; vol. 4, pp. 5960-5965; Nov. 4, 2002.*

Carter, C. "A Cavity Ring-Down Spectroscopy Mercury Continuous Emission Monitor"; Quarterly Technical Progress Report; [retrieved on Feb. 14, 2008];Jun. 30, 2003 Retrieved from the Internet:<URL:http://www.osti.gov/bridge/servelets/purl/821847-ORPLqs/native/821847.pdf>.*

* cited by examiner

Fig. 1 Experimental Setup

Fig.2 Cavity Modes and Ring-down Decay Rates

Fig. 3 Ringdown Distributions

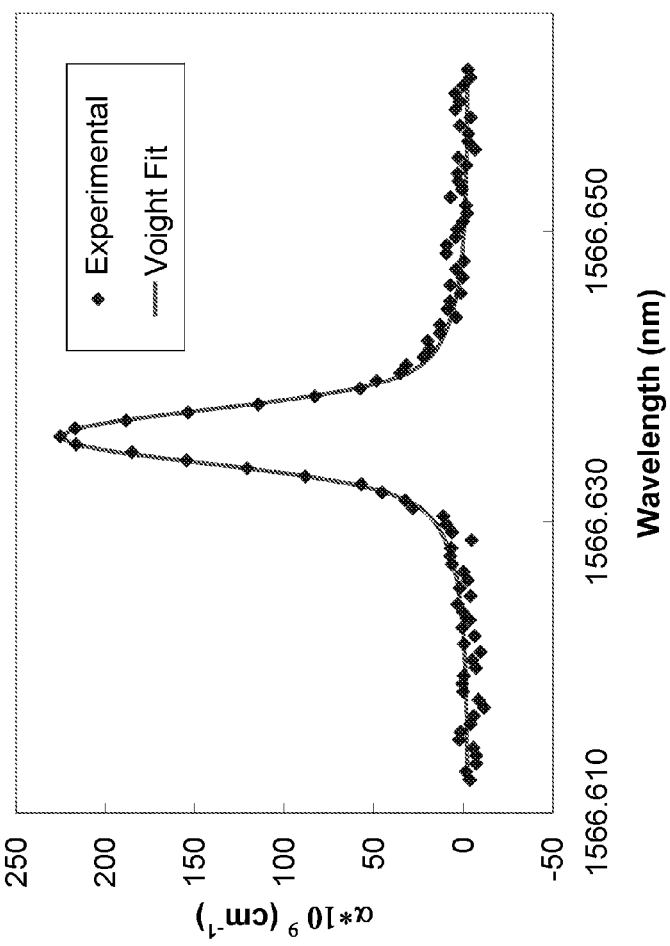
Fig. 5a Spectral Fits
- Molecular parameters from HITRAN 96, GEISA, and our own simulations.
$$x_j = \frac{\alpha(\lambda)}{Sg\rho}$$
$$\alpha(\lambda) = \frac{\tau_{empty} - \tau_\lambda}{c \cdot \tau_{empty} \cdot \tau_\lambda}$$

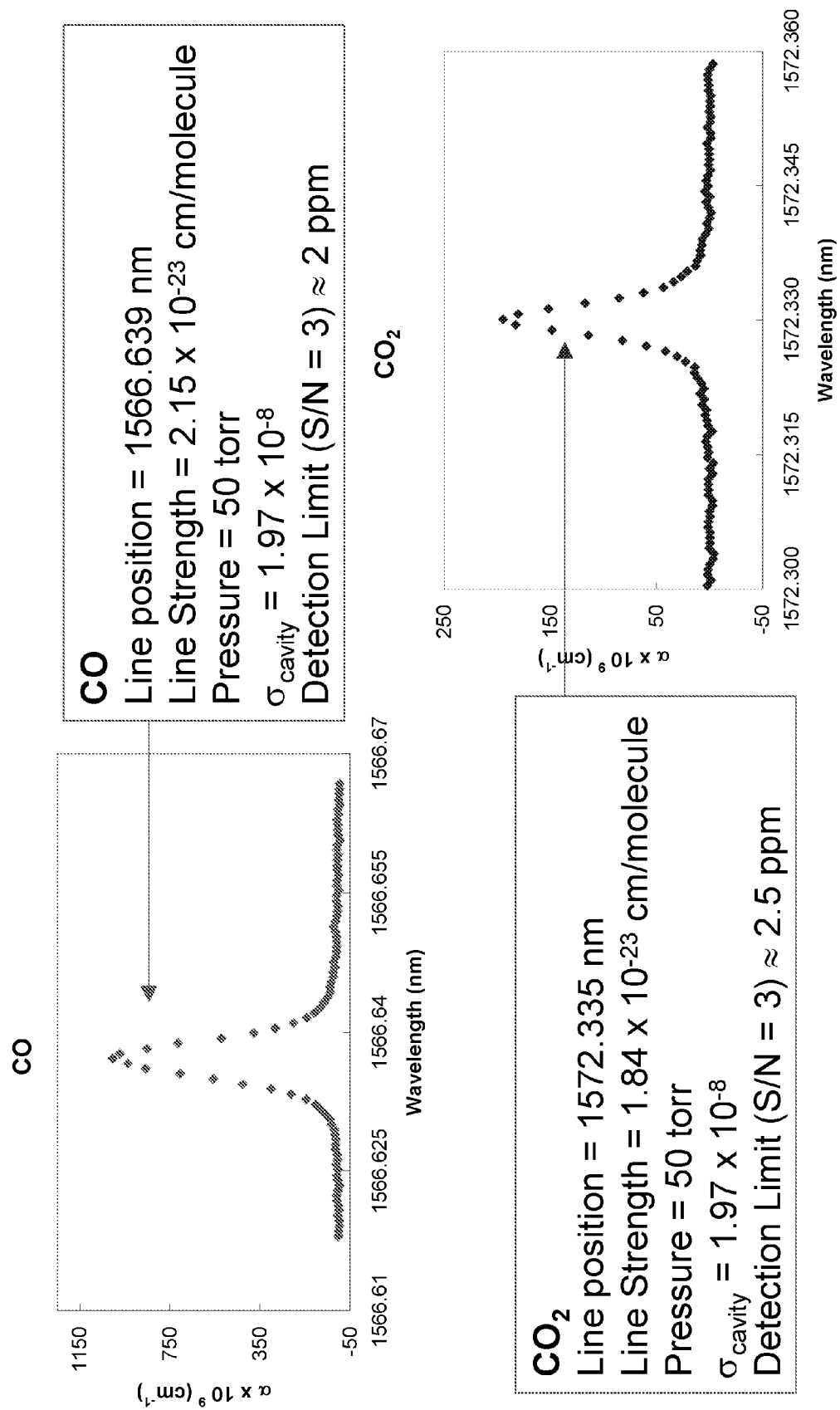
Fig.5b CO and $CO_2$ results

Detector Signal
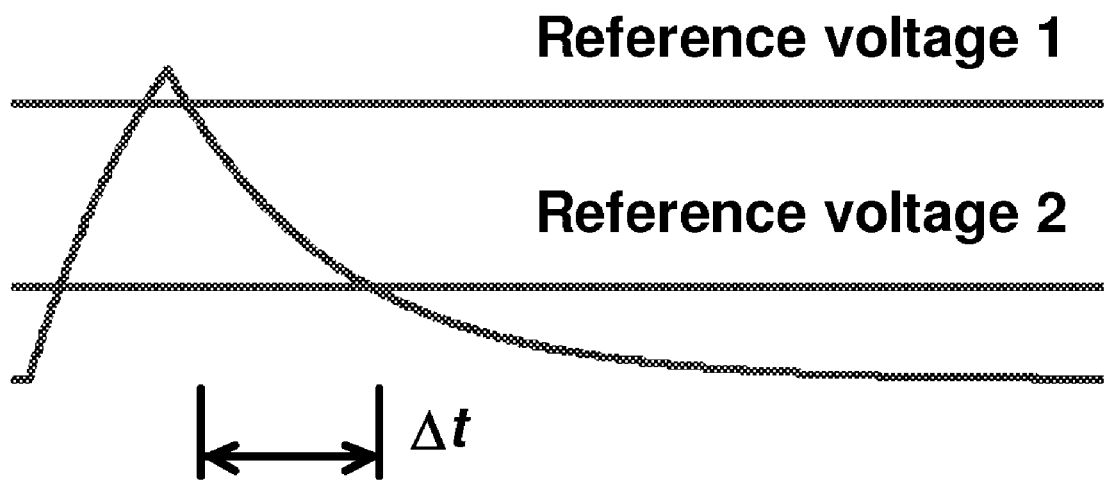
Voltage Ramp
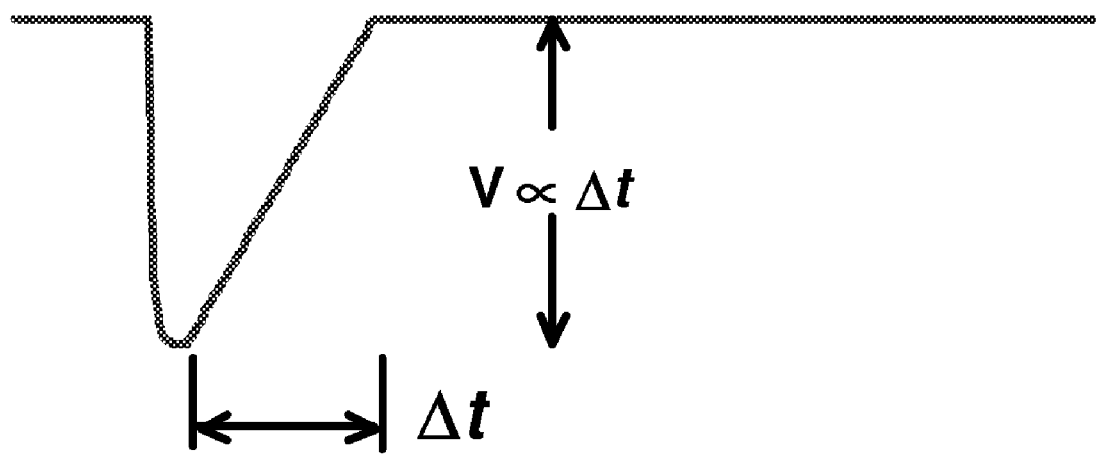
Fig. 7

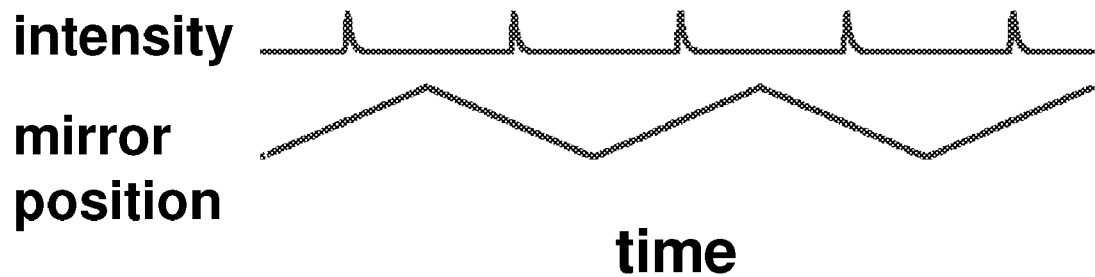
Fig. 8

(a)
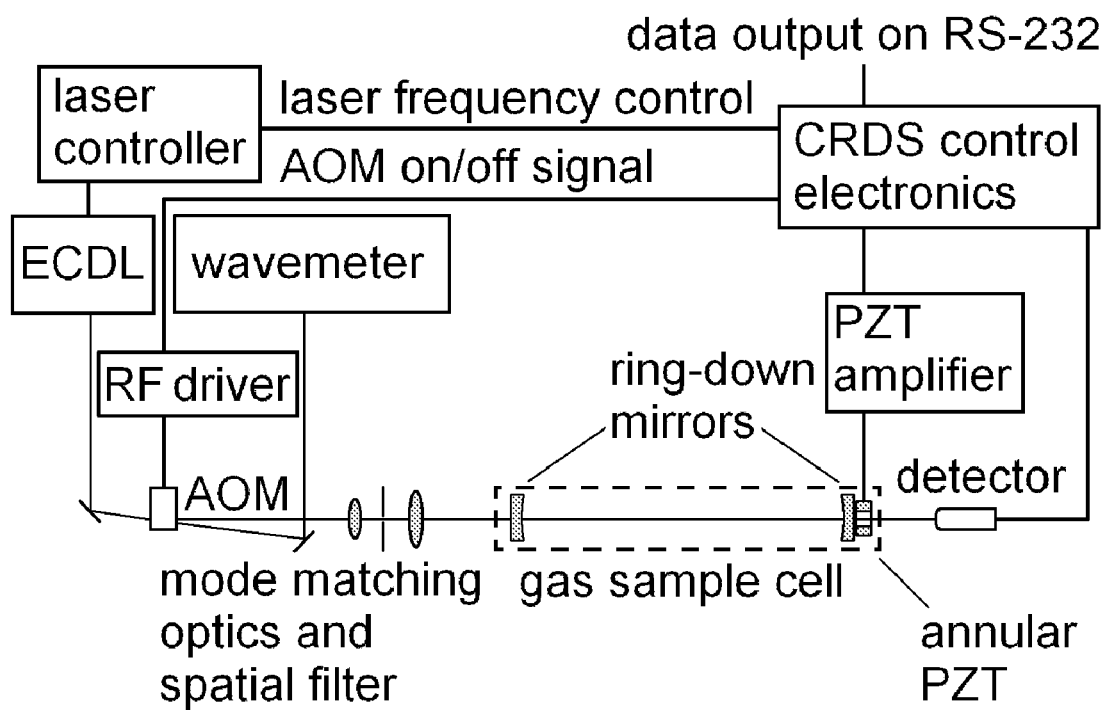
(b)
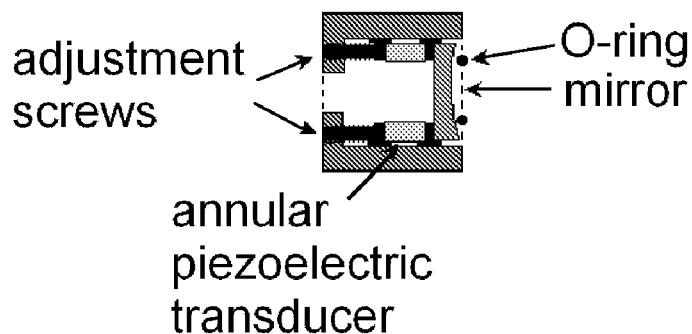
Fig. 10

Product/Prototype

US 7,569,823 B2

COMPACT NEAR-IR AND MID-IR CAVITY RING DOWN SPECTROSCOPY DEVICE

PRIORITY INFORMATION

This application claims the benefit under 35 USC 119 of the filing date of the application, U.S. Ser. No. 60/866,181, filed Nov. 16, 2006, and as a continuation-in-part under 35 USC 120 of the filing date of the application U.S. Ser. No. 11/558,445 filed Nov. 10, 2006, now U.S. Pat. No. 7,541,586.

FIELD OF THE INVENTION

This invention relates to a compact continuous wave cavity ring down spectrometer for detection and measurement of trace species in a sample gas.

BACKGROUND OF THE INVENTION

The availability of compact and efficient spectroscopic quality tunable diode lasers has generated interest in the development of portable optical diagnostic instruments. Advances in the communications industry have produced inexpensive, reliable and robust diode lasers in the near infrared. In the area of trace gas detection, the use of sensitive in situ diagnostics enables improved field measurements and better process control in a wide variety of applications, such as environmental monitoring, process control, and medical diagnostics.

Many technologies are available for measuring trace species of a sample gas, but there are tradeoffs between accuracy, sensitivity, selectivity, size and cost. Absorption spectra resulting from methods such as tunable diode laser absorption spectroscopy (TDLAS) with wavelength or frequency modulation, and FTIR are usually easy to interpret and are not limited by species selectivity. However, these are generally orders of magnitude less sensitive than laboratory techniques such as GC/MS, laser induced fluorescence (LIF), and photoacoustic spectroscopy (PA).

Cavity ringdown spectroscopy (CRDS) is a highly sensitive linear absorption technique that is capable of monitoring a wide range of species. U.S. Pat. No. 6,842,548 to Loock et al. discloses a standard method and apparatus for measuring one or more optical properties of a test medium, comprising providing an optical waveguide loop comprising a test medium, illuminating the optical waveguide loop with a plurality of light pulses, and detecting roundtrips of the light pulses at one or more locations along the loop, wherein the detected light pulses are indicative of one or more optical properties of the test medium. Preferably, ring-down time of said light pulses is determined. The invention provides measures of optical properties such as absorbance and refractive index of a test medium such as a gas, a liquid, and a solid material.

Although most often performed using pulsed lasers, a number of groups are now exploring the use of cw, solid state lasers in CRDS. Lehmann et al., Meijer et al., and Romanini et al. were the first to use continuous-wave lasers for CRDS. In cw-CRDS a laser beam probes an optical cavity constructed of two highly reflective mirrors (R>0.9999). Light builds up in the cavity when the wavelength matches a cavity transmission mode. The frequency spacing between cavity transmission modes is the free spectral range (FSR), $$FSR = 1/L_{rt}$$

where $L_{rt}$ is the round trip pathlength of the cavity in centimeters. Once the intensity reaches a preset level, the source is terminated and a ringdown event is captured. Initial attempts at cw-CRDS employed locking the cavity length to the laser frequency to ensure the buildup of light. U.S. Pat. No. 5,528,040 to Lehman discloses an apparatus for detection and measurement of trace species in a sample gas. A ring down cavity cell is filled with the sample gas. A continuous wave laser emits radiation, which is directed from the continuous wave laser to the ring down cavity cell where it resonates. A photodetector measures radiation levels resonated by the ring down cavity cell and produces a corresponding signal. The decay rate of the ring down cavity cell is calculated from the signal produced by the photodetector and is used to determine the level of trace species in the sample gas.

Romanini et al. modulated the cavity length to scan several transmission modes of the cavity across the laser frequency. This allowed for the buildup of light in the cavity at any frequency without the complications of cavity locking. U.S. Pat. No. 6,084,682 to Zare discloses distinct locking and sampling light beams are used in a cavity ring-down spectroscopy (CRDS) system to perform multiple ring-down measurements while the laser and ring-down cavity are continuously locked. The sampling and locking light beams have different frequencies, to ensure that the sampling and locking light are decoupled within the cavity. Preferably, the ring-down cavity is ring-shaped, the sampling light is s-polarized, and the locking light is p-polarized. Transmitted sampling light is used for ring-down measurements, while reflected locking light is used for locking in a Pound-Drever scheme.

An acousto-optic modulator (AOM) has been used in conjunction with a threshold circuit to shut off the light source when sufficient buildup occurred. Paldus et al. showed that an additional benefit of using an AOM is that the first order beam generated by the device is frequency shifted, so any light that is fed back to the laser diode source will not result in stabilization problems caused by optical feedback. Paldus et al. also developed a ring configuration which allowed for locking the cavity to the laser frequency, thus increasing the precision in ringdowns and improving detection limits.

U.S. Pat. No. 5,903,358 to Zare discloses a cavity ring down spectroscopy (CRDS) system uses a free-running continuous wave (c.w.) diode laser stabilized by frequency-shifted optical feedback in the presence of strong reflections from a high-finesse Fabry-Perot resonator. The frequency-shifted feedback stabilization eliminates the need for tightly controlling the relative positions of the laser and resonator. Non-frequency-shifted feedback is used for linewidth broadening. An acousto-optic modulator placed between the diode laser output and the resonator input frequency-shifts light reflected by the resonator input, causing the laser to cycle in phase with a period equal to the inverse of the frequency-shift. The laser diode linewidth can be stabilized from several MHz for high resolution spectroscopy of species at low pressures, to several hundred MHz for lower resolution spectroscopy of species at atmospheric pressures.

U.S. Pat. No. 5,815,277 to Zare discloses the use of light that is coupled into a cavity ring down spectroscopy (CRDS) resonant cavity by using an acousto-optic modulator. The AOM allows in-coupling efficiencies in excess of 40%, which is two to three orders of magnitude higher than in conventional systems using a cavity mirror for in-coupling. The AOM shutoff time is shorter than the roundtrip time of the cavity. The higher light intensities lead to a reduction in shot noise, and allow the use of relatively insensitive but fast-responding detectors such as photovoltaic detectors. Other deflection devices such as electro-optic modulators or elements used in conventional Q-switching may be used instead of the AOM. The method is particularly useful in the mid-infrared, far-infrared, and ultraviolet wavelength ranges, for which moderately reflecting input mirrors are not widely available.

Sensitivity is also an issue. U.S. Pat. No. 6,727,492 to Ye et al. discloses an ac technique for cavity ringdown spectroscopy permits $1\times10^{-10}$ absorption sensitivity with microwatt light power. Two cavity modes are provided temporally out of phase such that when one mode is decaying, the other mode is rising. The system and method provides a quick comparison between on-resonance and off-resonance modes and enables sensitivities that approach the shot-noise limit.

Others have tried various data manipulations to improve results. U.S. Pat. No. 6,915,240 to Rabinowitz discloses A novel system and method for data reduction for improved exponential decay rate measurement in the present of excess low frequency noise. The system and method fit the tail of a record to a straight line wherein the straight line is extrapolated to the entire record and then subtracted from the initial data points before a logarithmic transformation is taken.

Fieldable methods for detecting and measuring chemical hazards are needed. However, instruments that operate in the field must be able to withstand mechanical vibration and shock, and produce accurate and reliable results.

SUMMARY OF THE INVENTION

In a preferred embodiment, a compact cavity ring down spectroscopy apparatus for detection and measurement of trace species in a sample gas is provided, which comprises: a housing for said apparatus; a tunable solid-state continuous-wave mid-infrared PPLN OPO laser within said housing; an acousto-optic modulator in optical communication with said laser for steering a first order diffraction beam of said laser and for interrupting said beam when resonance is achieved; a ring down resonant cavity within the housing for holding a sample gas, said cavity cell receiving said first order diffraction beam of said laser and comprising at least two high-reflectivity mirrors, wherein said mirrors define an intracavity light path and one of said mirrors is a movable tuning mirror; a piezo transducer drive attached to the tuning mirror for modulating cavity length to maintain resonance between the laser frequency and cavity modes; and a photo-detector within said housing, for receiving said beam from the cavity and for generating a resonance signal and a voltage decay (ring down) signal, thereby measuring an interaction of said sample with said intracavity beam.

In another preferred embodiment, a compact cavity ring down spectroscopy apparatus for detection and measurement of trace species in a sample gas is provided, and which comprises: a housing for said apparatus; a tunable low-power solid-state continuous wave near-infrared diode laser within said housing; an acousto-optic modulator in optical communication with said laser for steering a first order diffraction beam of said laser and for interrupting said beam when resonance is achieved; a ring down resonant cavity within the housing for holding a sample gas, said cavity cell receiving said first order diffraction beam of said laser and comprising at least two high-reflectivity mirrors, wherein said mirrors define an intracavity light path and one of said mirrors is a movable tuning mirror; a piezo transducer drive attached to the tuning mirror for modulating cavity length to maintain resonance between the laser frequency and cavity modes; a photo-detector within said housing, for receiving said beam from the cavity and for generating a resonance signal and a voltage decay (ring down) signal, thereby measuring an interaction of said sample with said intracavity beam; and a microprocessor for reducing the periodic noise in the voltage decay signal by recording the cw-CRD voltage decay signals as data and subjecting the data to an algorithm selected from either an averaging the interquartile range of the data, or a cluster analysis.

In a preferred embodiment, the cavity has 4 mirrors in a bowtie configuration.

In another preferred embodiment, the trace species of the sample gas is selected from the group consisting of: HCHO, H2S, METHYL MERCAPTAN, CO2, CO, HCN, HCl, NH3, C2H2.

In another preferred embodiment, the trace species of the sample gas can be large when using mid-IR lasers and may include trace species such sarin, VX, mustard gas, arsine, phosgene, tear and pepper gases, explosives like TNT and other nitrogen-based explosives, and incapacitating agents such as B2.

Another preferred embodiment of the mid-IR CRDS apparatus further comprises a microprocessor for reducing the periodic noise in the voltage decay signal by recording the cw-CRD voltage decay signals as data and subjecting the data to an algorithm selected from either an averaging the interquartile range of the data, or a cluster analysis.

In yet another preferred embodiment, the optical communication is optical fiber based.

For a desktop apparatus, the foot print of this prototype would be between about 6" to about 12" wide, preferably 8.5" wide, by about 5" to about 8" deep, preferably 6.5" deep, by about 5" to about 8" tall, preferably 4" tall, as a bench-top device. In a preferred embodiment, the device weighs about 5 to about 12 pounds, and preferably weighing about 6 pounds. Further, it can be easily configured to fit in a 2U box for standard 19" rack.

Advances in the communications industry have produced inexpensive, reliable and robust diode lasers in the near infrared, thus providing one preferred embodiment of the inventive CRDS apparatus to be uniquely compact and portable, and having low power consumption. These features are highly advantageous in a number of situations and allow the sensitivity of CRDS to be used in many novel approaches.

The inventive subject matter also includes a method for determining an exponential decay rate of a signal in a cavity ring down spectroscopic analysis, said method comprising: providing a ring down resonant cavity for holding a sample gas, wherein the cavity has at least one tunable mirror; illuminating the cavity with a tunable laser;

matching the cavity length to the laser frequency by moving the tunable mirror until resonance is detected; interrupting the laser beam; detecting one or more decay signals; and steps of: recording the decay signals as data; and subjecting the data to an algorithm selected from an averaging of the interquartile range, wherein discarding the upper and lower quartiles before averaging the data values reduces the periodic noise in cw-CRD spectra when using cavity modulation, or a cluster analysis to reduce the periodic noise in cw-CRD spectra when using cavity modulation.

In alternative preferred embodiments, the tunable mirror comprises a high reflectivity mirror attached to a piezo transducer driver, or the tunable laser is a continuous wave laser, or the tunable laser is a continuous wave near-infrared laser, or interrupting the laser beam comprises switching off an acousto-optic modulator.

In a further preferred embodiment, the decay signals generated during resonance number between about 1 kHz to about 20 kHz, and more preferably between about 10 kHz to about 20 kHz.

Another preferred embodiment of the inventive method further comprises the step of: vi) maintaining resonance within the cavity by switching the AOM back on and monitoring the cavity for resonance, wherein decay signals continue to be detected if resonance is detected within the cavity, and wherein cavity modulation by moving the tunable mirror is performed if resonance is not detected within the cavity.

Another preferred instrument is uniquely compact and portable, and has low power consumption. These features are highly advantageous in a number of situations including monitoring of HCHO, H2S, METHYL MERCAPTAN, CO2, CO, HCN, HCl, NH3, C2H2 (for both near-IR and mid-IR), and for monitoring sarin, VX, HCN, mustard gas, arsine, phosgene, tear and pepper gases, explosives like TNT, and incapacitating agents such as B2 (for mid-IR only).

BRIEF DESCRIPTION OF THE DRAWINGS

FIG. 5. A series of $CO_2$ measurements obtained while varying the pressure and maintaining concentration. The 80, 40 and 20 torr peaks were fit with a voigt lineshape while the 5 torr peak was fit with a gaussian lineshape. The fit determined concentration was 453 ppm with a standard deviation of 7 ppm.

Analog Figures

FIG. 7: The analog decay constant measurement. As the detector signal exceeds reference voltage 1, a voltage ramp is reset to zero. The voltage increases linearly during the time ⊠t that the detector signal decays between the two reference voltages. The final voltage reached is proportional to the decay time of the signal.

FIG. 8: A comparison of the sweep and hold procedure with continuous sweeping. The continuous sweep (top) produces resonance only at discrete points in the sweep. The sweep and hold method (bottom) pauses the sweep at resonance and allows for the generation of a burst of ring-downs; the cavity mirrors are also held stationary during the measurement period. This allows sensitivity to greater than or equal to 1 KHz.

Figure 9:
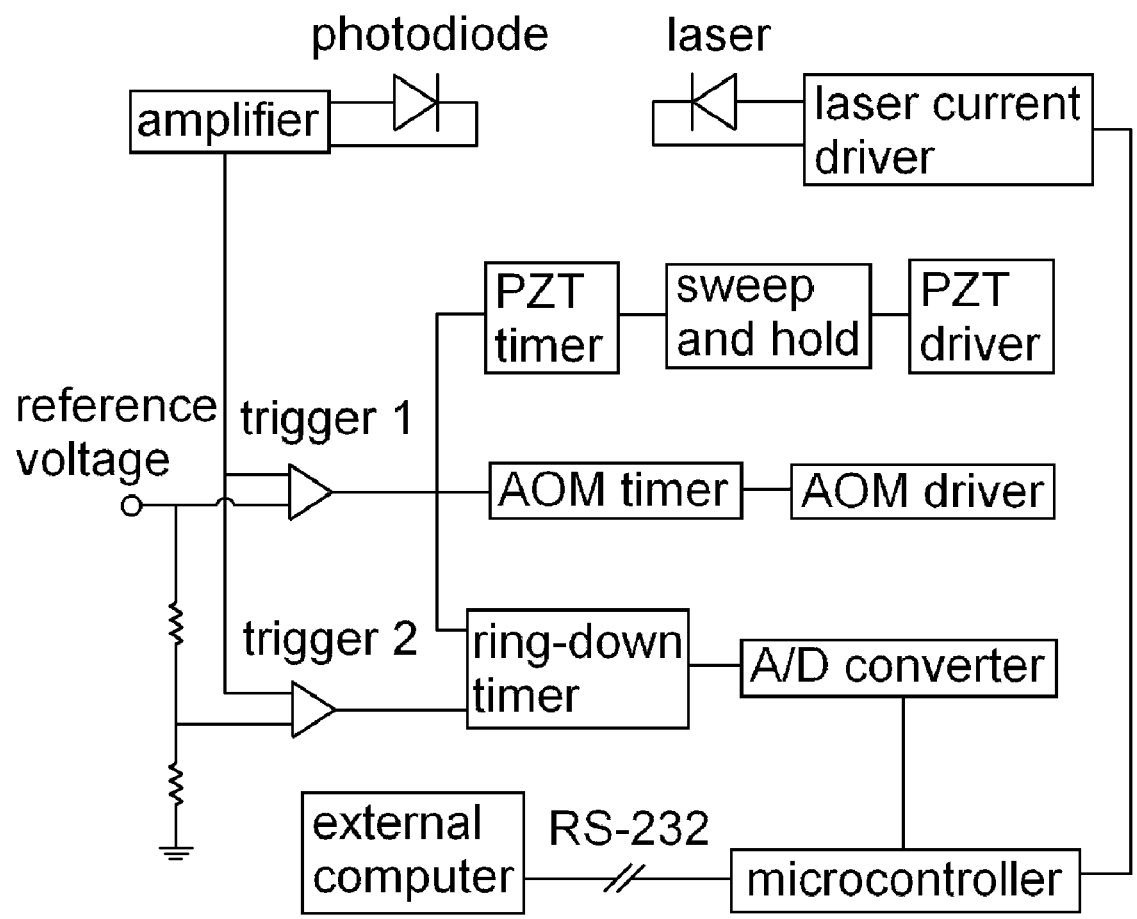

FIG. 9: The electronic block diagram: trigger 1 pauses the sweep and hold circuit, turns the AOM off, and initiates the analog ring-down timer. Trigger 2 completes the ring-down measurement. The measurement is recorded using an A/D converter and stored in memory. A microcontroller increments the laser wavelength after a predetermined number of ring-downs and sends data to an external computer.

FIG. 10: Cavity ring-down setup: (a) experimental layout and (b) mirror mount detail. The custom mirror mounts mate with standard CF fittings on the gas sample cell.

Figure 11:
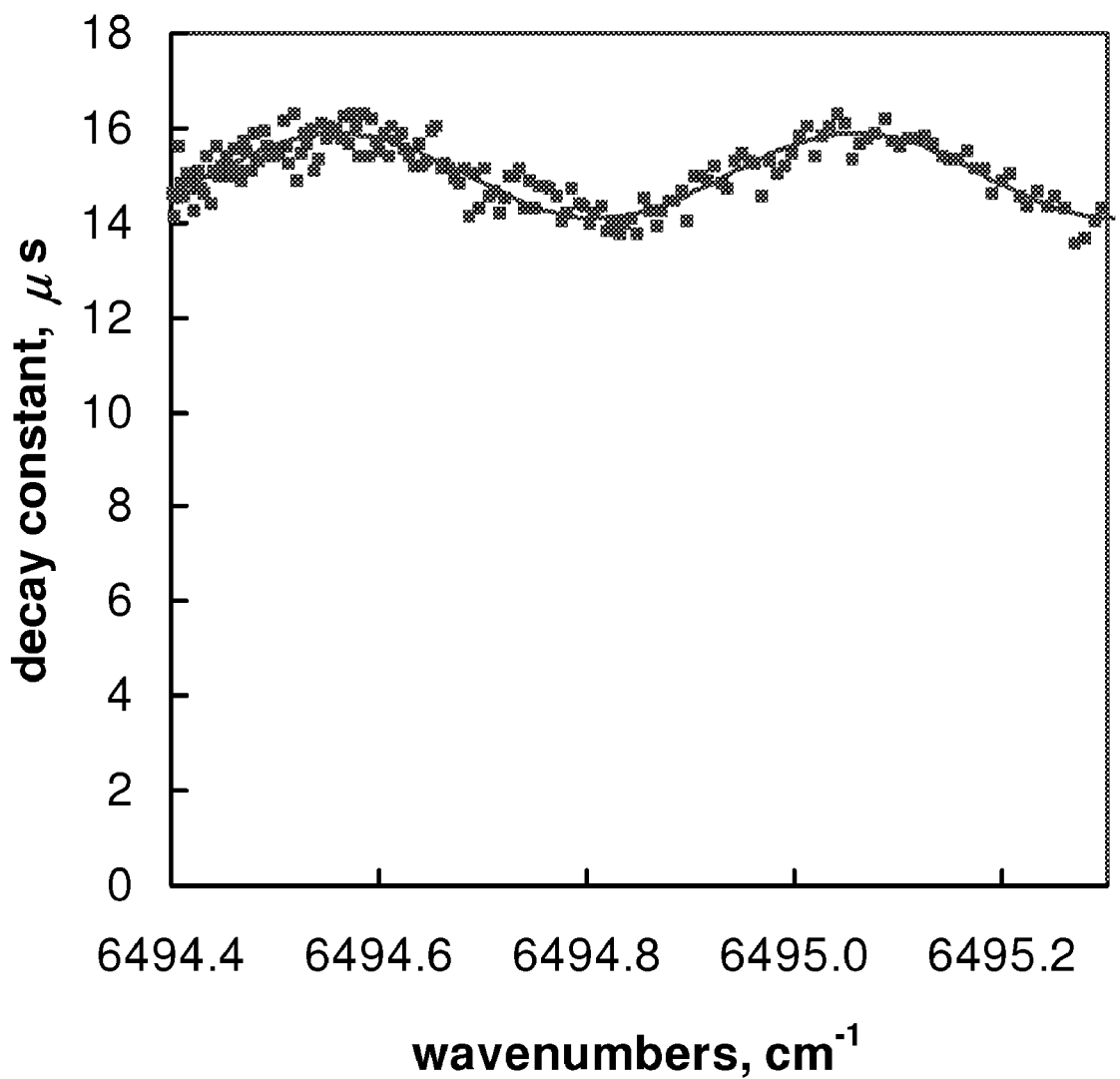

FIG. 11: Sinusoidal oscillation of decay time with wavelength in an empty cavity, due to cavity mirrors behaving as etalons. Data points are shown as dots and a sinusoidal fit is shown as a solid line. This is an indication of the quality of the mirror, an aspect which is addressed by the present invention. The variation is caused by reflection back from the back side of the mirror.

Figure 12:
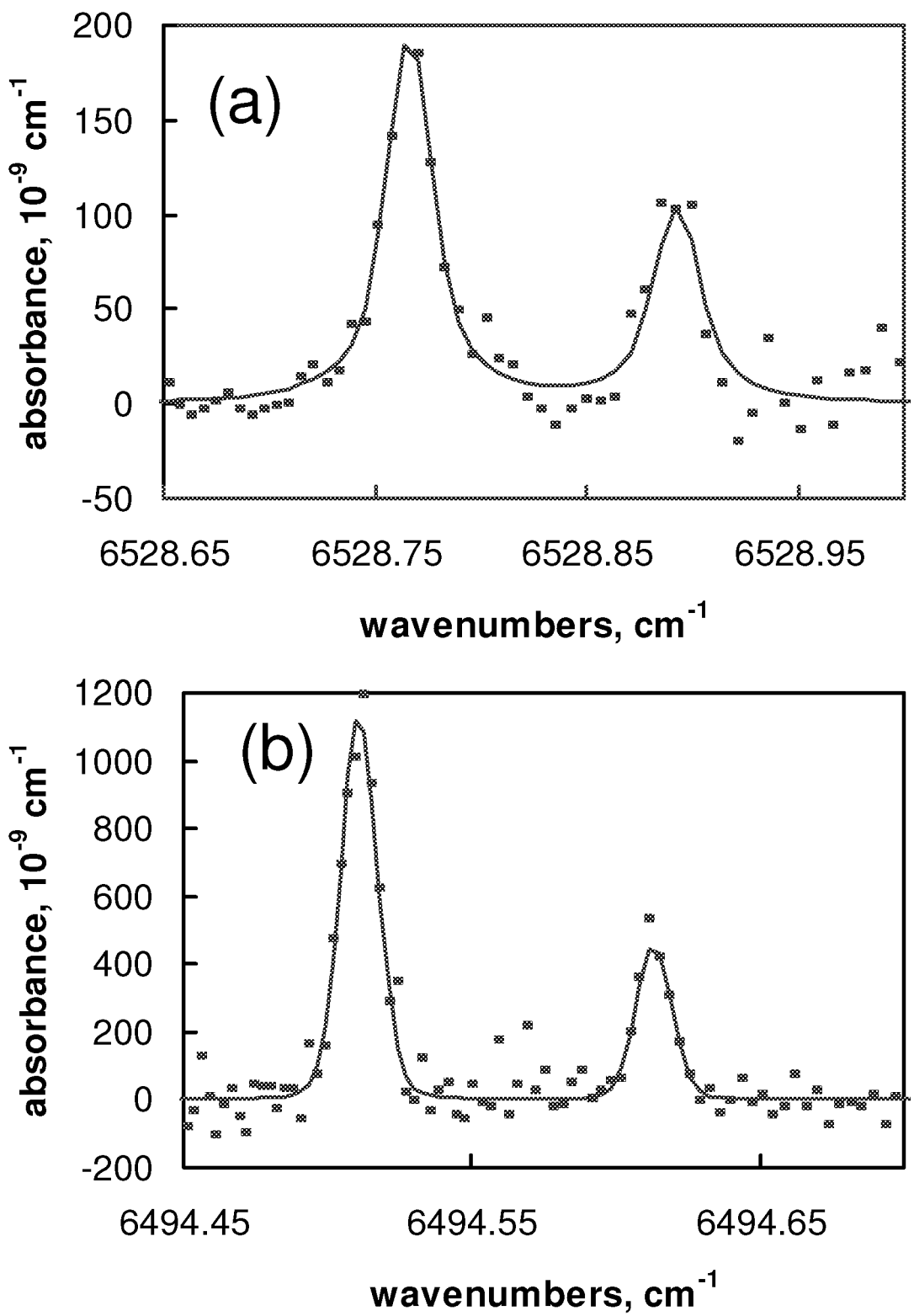
Figure 13:
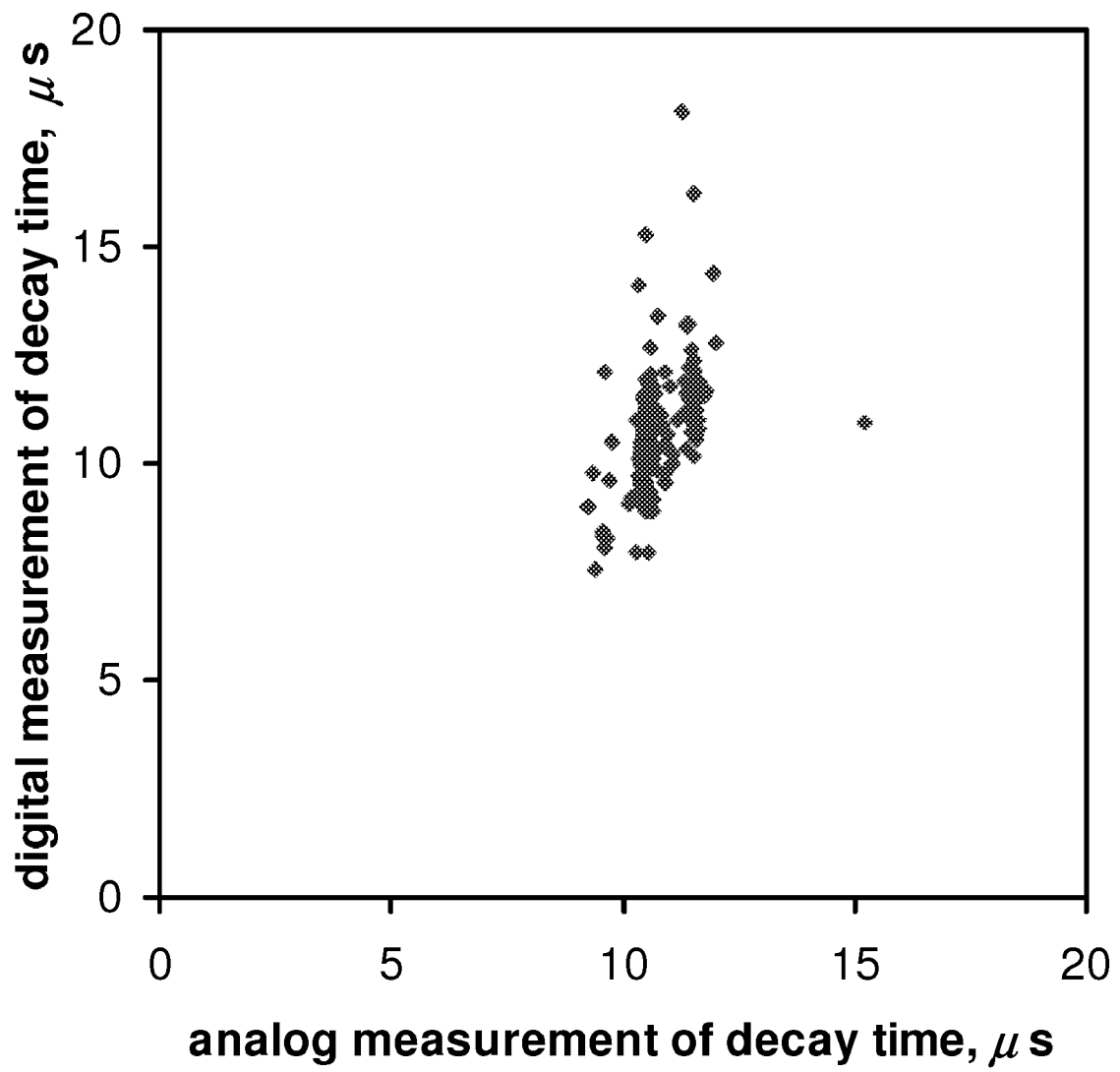

FIG. 12: (a) 1.7 ppm ammonia in air at 50 Torr; data points are shown as dots and fit is shown as a solid line (b) 28 ppm acetylene in air at 50 Torr; data points are shown as dots and fit is shown as a solid line FIG. 13: A comparison of decay times acquired by the analog measurement scheme with those acquired by a high speed analog to digital converter. Poor correlation between the two measurement schemes is a possible indication of nonexponential decay. Note the two groupings of datapoints which show analog (L) and digital (R).

Figure 14:
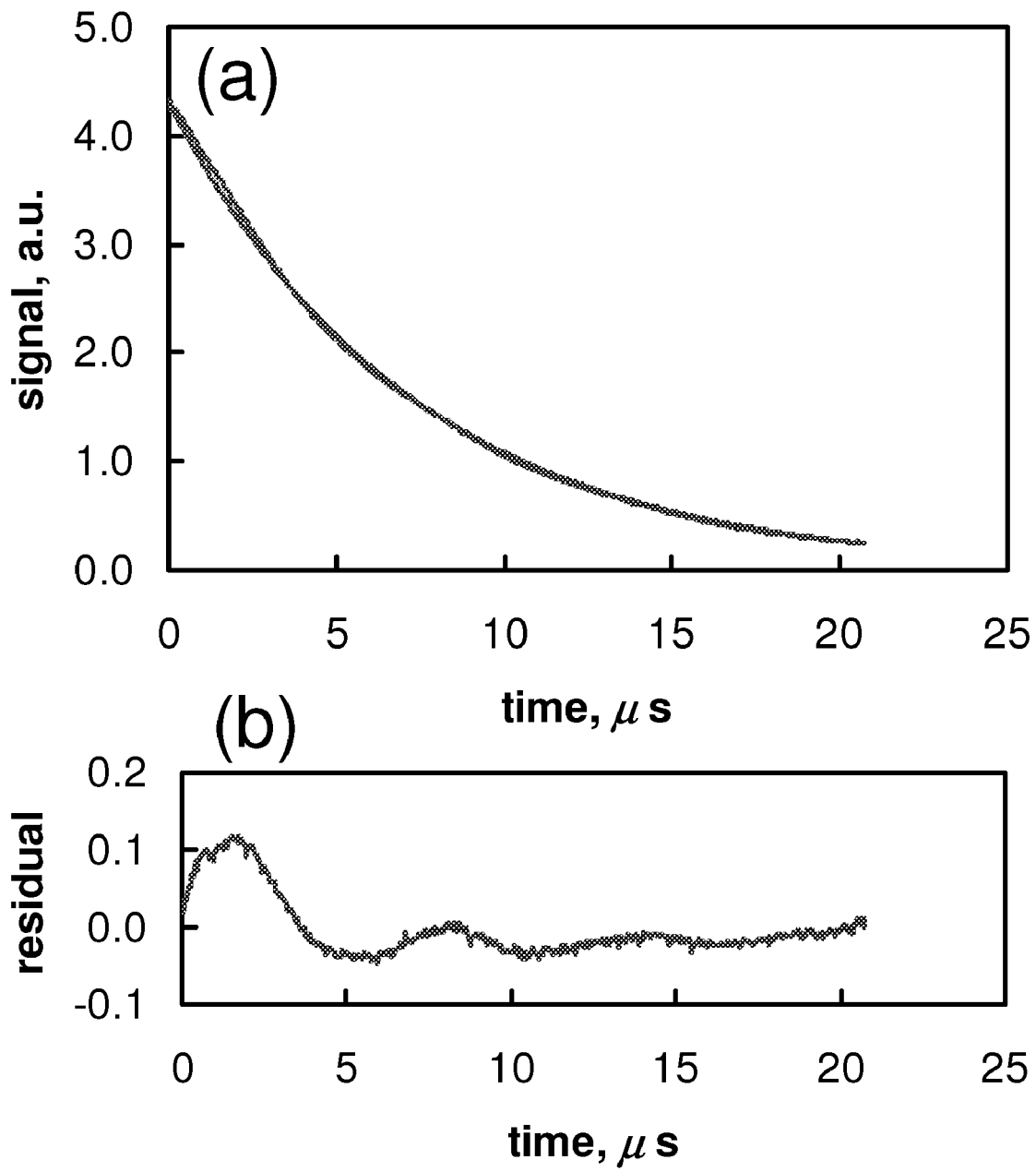

FIG. 14: (a) Decay signal fit to an exponential and (b) the corresponding residual. Note oscillations in the residual, indicative of nonexponential decay.

Figure 15A:
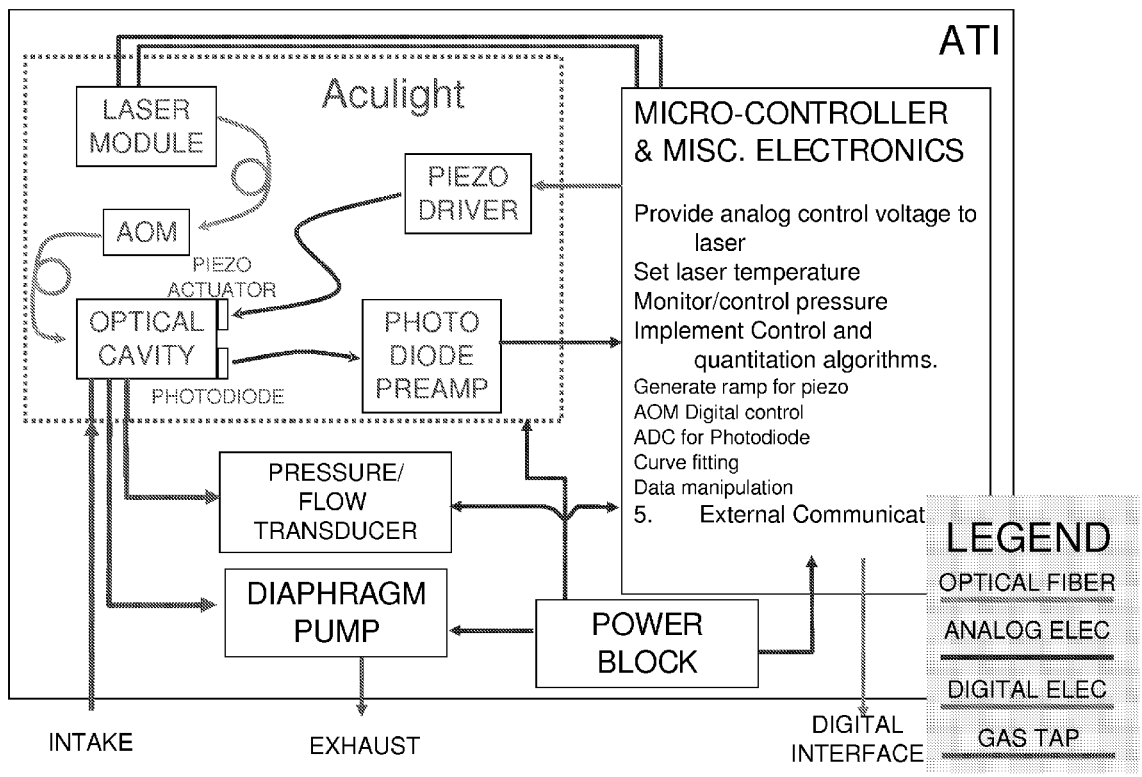
Figure 15B:
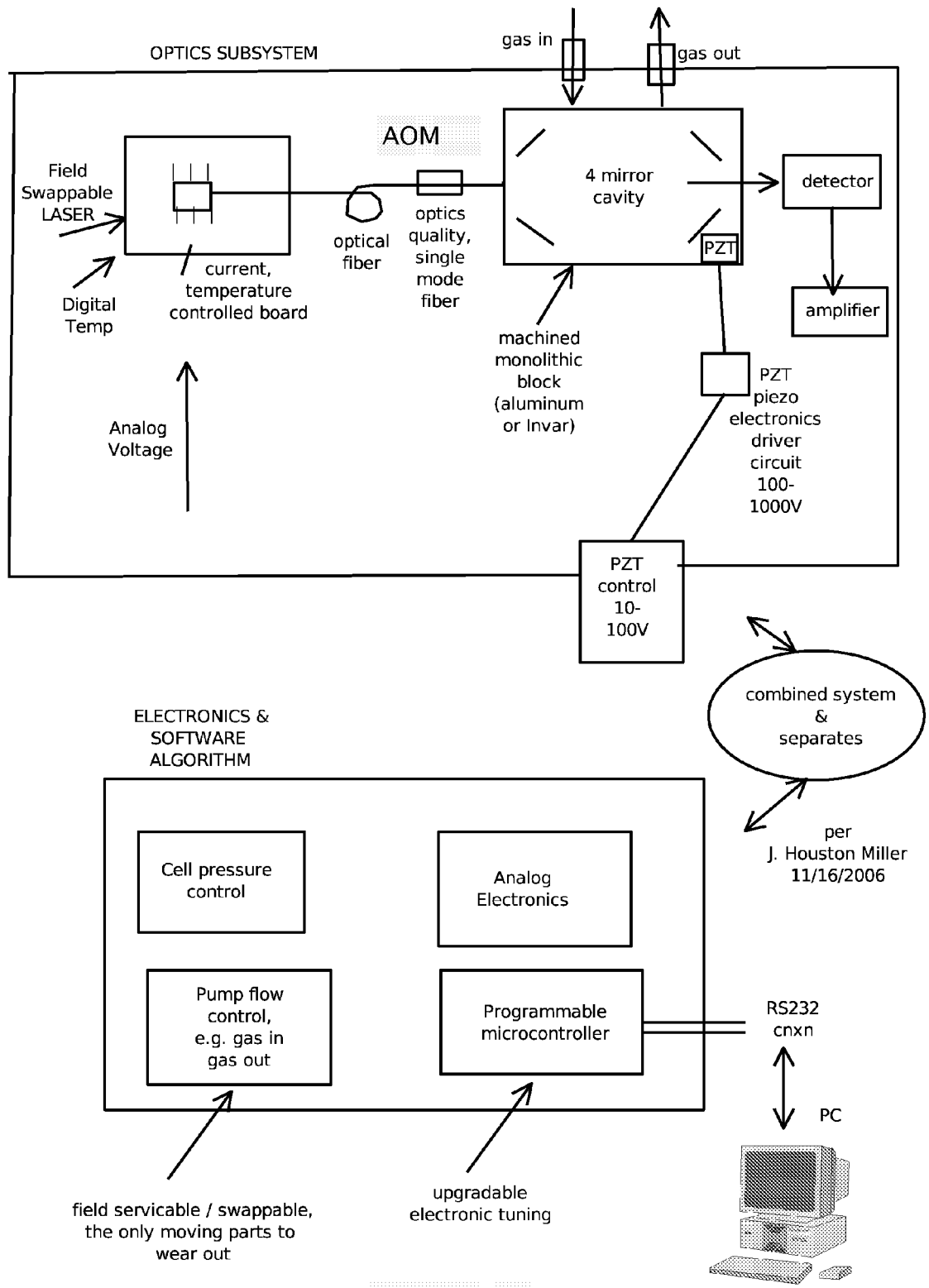

FIG. 15 is a description of one preferred commercial embodiment showing an optics subsystem and the electronic and software algorithm system.

Figure 16:
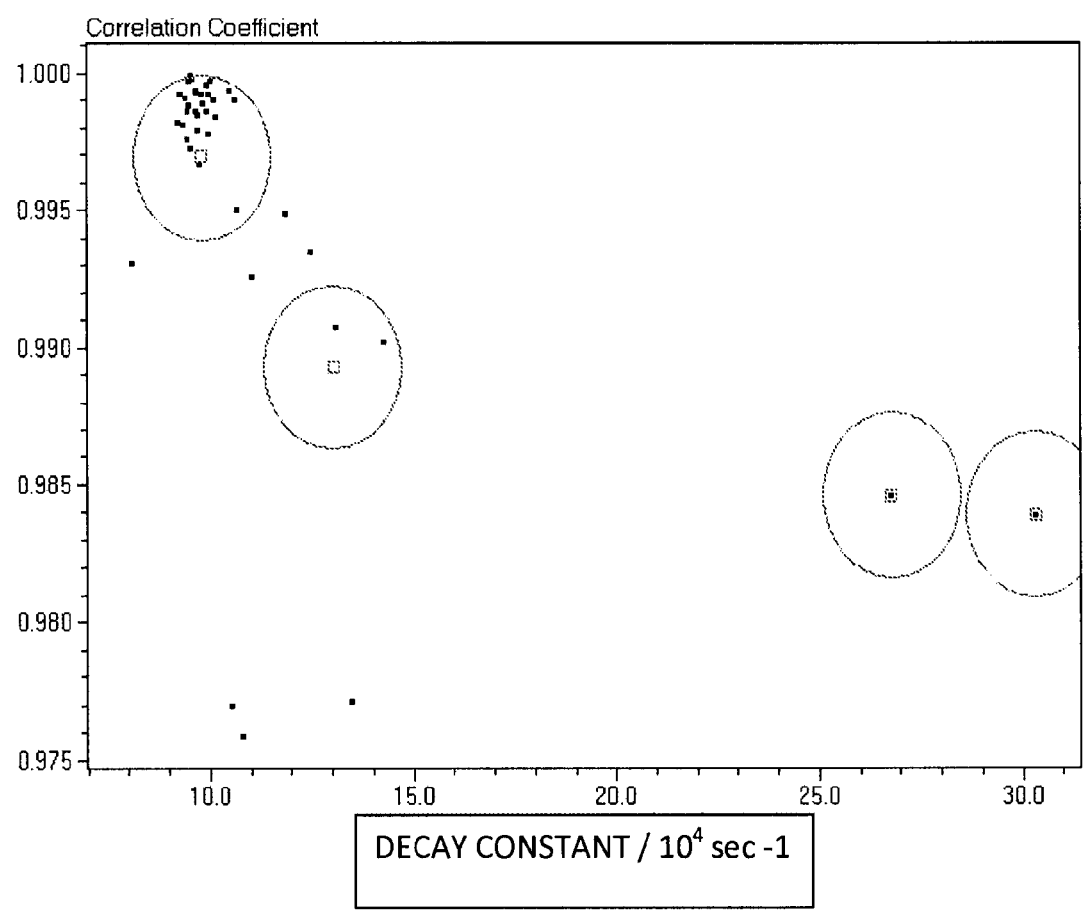

FIG. 16 is a graph of a Cluster Analysis and shows a series of ringdowns that are fit and a 2 dimensional Agglomerate clustering algorithm used, to plot decay constant ($\div 10^4$) in units of sec−1 and fit quality (correlation coefficient.

DETAILED DESCRIPTION OF THE PREFERRED EMBODIMENTS

CRDS

Cavity ring-down spectroscopy is a sensitive absorption measurement technique for trace gas detection. A measurement consists of observing the rate of decay of light in a high finesse optical cavity, and then relating this rate of decay to the concentration of absorbing species. Two or more high reflectivity dielectric mirrors are arranged to form a stable optical cavity. The finite transmission of the dielectric coatings allows light to be introduced into the cavity through one of these mirrors. At some time t=0, the laser is switched off. The light remaining in the cavity then decays with time due to a combination of mirror losses and absorption losses. A detector measuring the intensity of light transmitted by the cavity is then used to measure the rate of its decay. The absorbance at a given wavelength, $\alpha(\lambda)$, of gas inside the cavity is related to the decay time at that wavelength, $\tau_\lambda$, through $$\alpha(\lambda) = \frac{\tau_c - \tau_\lambda}{c\tau_c\tau_\lambda},$$

where $\tau_c$ is a measurement of the decay time of the cavity in the absence of any absorption and c is the speed of light. This measurement may be made by tuning the laser a few spectral line widths away from the absorption feature of interest. It is assumed that the cavity losses vary much more slowly with wavelength than does the molecular transition. The concentration of the absorbing species may then be written in terms of the absorbance as $$x = \frac{\alpha(\lambda)}{Sg\rho},$$

where S is the line strength, g is a line shape factor, and ρ is the density of gas inside the cavity. A significant advantage of this technique over other types of absorption spectroscopy is that the decay time depends solely on the optical properties of the cavity and is therefore independent of fluctuations in the laser intensity.

cw-CRDS

The cavity ring-down technique was originally developed using high power pulsed lasers. Modifications to the original technique have made CRDS measurements possible using low power continuous wave lasers. In addition to reduced power requirements, the use of narrow line width cw sources also results in higher spectral resolution. When the laser line width is smaller than the free spectral range of the cavity, only a single longitudinal mode of the cavity is excited. The ultimate resolution of the spectrometer is then determined by the line width of the cavity mode, which may be several orders of magnitude smaller than that of the laser. However, some means of matching the laser frequency to a mode of the cavity is required; either the laser or the cavity must be adjusted to produce overlap between the laser output and a cavity mode. Meijer et al. reported using natural thermal and mechanical instabilities present in the cavity to produce random coincidences between the laser frequency and a cavity mode. Rempe et al., Romanini et al., and He et al. each describe slightly differing methods of modulating the cavity length with a piezoelectric transducer in order to produce periodic matches. Paldus et al. have developed a means of actively locking the cavity length to match the laser frequency using a frequency tunable acousto-optic modulator (AOM).

AOM

Continuous wave CRDS also requires a fast switch, such as an AOM, to interrupt the input beam once sufficient light has been stored in the cavity to observe its decay. The switch must act on a time scale that is small compared to the decay time, which is on the order of 1 to 100 μs with the best available mirrors and cavity lengths on the order of a meter. Alternatively, the laser frequency may be quickly detuned to fall between two cavity modes. In the case of a diode laser, this can be achieved on the required time scale by a small change in the current supplied to the diode. The high finesse of the ring-down cavity ensures that virtually none of the detuned light is transmitted to the detector.

Data Capture

Once light has been successfully coupled into the cavity, the rate of decay of that light must be measured. A digital data acquisition scheme may be used, in which signals from a detector are recorded with a high-speed digitizer and then fit to an exponential decay with a standard curve fitting routine. While accurate, this method is computationally intensive, and can become the limiting factor in the data acquisition rate. Alternative analog methods of decay time measurement have been explored previously. Spence et al. use a simple analog computer in conjunction with a lock-in amplifier, a method best suited to a laser locked cavity where the ring-downs can be generated at a constant rate. Romanini and Lehmann make a two point measurement of the decay time using a boxcar averager. The boxcar is used to average the detector signal over two narrow windows separated by a fixed delay time of $\Delta t$. A comparison of these two averages allows a determination of the decay time to be made. This method does not require a locked cavity. However, for best accuracy, the delay time $\Delta t$ must be chosen in advance to be on the order of the decay constant. If the decay time varies significantly over the course of a spectral scan, as for example due to the presence of a relatively strong absorption line, the accuracy of the measurement will be reduced.

New Cavity Modulation and Ring Down Measurement Scheme

For the present invention, a cavity ring down spectrometer is provided that incorporates a new type of cavity modulation and ring-down measurement scheme, and its advantages are discussed. Spectra of ammonia and acetylene acquired using this arrangement are presented, and a comparison of ring-down measurements are made with measurements from a digital data acquisition card (Gage Applied Technologies CS1250).

Cavity Modulation—Mirror Displacement and Measurement Accuracy

One means of matching a mode of a ring-down cavity to a narrow line width source is by adjusting the cavity length. However, the resolution may be adversely affected when using a moving cavity mirror due to a Doppler shift of the light inside the cavity. In addition, nonexponential behavior of the decay signal may occur due to interference effects.

Consider a cavity of length L. Suppose a longitudinal mode is excited by light of frequency $v_0$, and the light source is then shut off to allow the cavity mode to decay. The order of the excited mode, m, is given by $$m = \frac{2Lv_0}{c},$$

where c is the speed of light. If one cavity mirror is moved at a speed s, the resonant frequency of the excited cavity mode, $v_c$, changes by $$v_c(t) = \frac{mc}{2(L+st)}; \frac{mc}{2L}\left(1 - \frac{st}{L}\right).$$

The frequency of light inside the cavity will also change due to a Doppler shift caused by reflections from a moving mirror. This Doppler shift alters the frequency a factor of $$\frac{c-s}{c}$$

per reflection. Reflections occur at a rate $$\frac{c}{L},$$

leading to a total frequency shift after a time t of $$v(t) = v_0 \frac{c-s}{c}^{\frac{ct}{L}} = \frac{mc}{2L}\frac{c-s}{c}^{\frac{ct}{L}}.$$

Assuming that $$\frac{s}{c} = 1,$$

this expression may be approximated, to first order, as $$v(t); \frac{mc}{2L}\left(1 - \frac{st}{L}\right),$$

which is identical to the expression given by equation (4) for the change in cavity mode frequency. Therefore, a cavity with a moving mirror shifts both the cavity mode frequency and the radiation frequency by the same amount. As a result, resonance is maintained even if the frequency shift due to cavity modulation exceeds the width of the cavity mode. Note that no assumption was made about the sign of the mirror velocity, so this derivation is applicable to both increasing and decreasing cavity length.

In order to maintain the resolution of the spectrometer, the mirror speed should be such that the frequency shift due to length modulation over the decay time τ is small compared to the width of the cavity mode. A high finesse cavity with mirror reflectivity R has modes with a width, Δν, given by $$\Delta v = \frac{c(1-R)}{2\pi L \sqrt{R}}.$$

From expressions (4) or (6), the mirror speed which produces a frequency shift of Δν after a time τ can be found as $$\frac{mcv\tau}{2L^2} = \frac{c(1-R)}{2\pi L \sqrt{R}},$$

or equivalently by $$v = \frac{L(1-R)}{\pi m\tau \sqrt{R}} = \frac{c(1-R)}{2\pi \tau v \sqrt{R}}.$$

Considering only the losses due to finite reflectivity, the decay time may be written as $$\tau = \frac{L}{c(1-R)},$$

allowing equation (9) to be rewritten as $$v = \frac{c^2(1-R)^2}{2\pi L v \sqrt{R}}.$$

This is the mirror speed that will produce a frequency shift after one decay time equal to the cavity line width. As an example, for the cavity used in our experiments, L=0.5 m, R=0.9999, and λ=1.53 μm. The line width of the cavity is then found from equation (7) to be 9.6 kHz, and the mirror speed calculated from equation (11) is 1.5 μm/s. Modulation over one free spectral range at this speed, requiring a back and forth mirror displacement of λ/2, would then occur at a rate of 1 Hz. This is the modulation rate at which the Doppler shift is equal to the line width of the cavity. Modulation at a higher frequency or over a greater displacement will produce a corresponding decrease in resolution. Although cavity line widths on the order of kilohertz are much narrower than typical thermally and collisionally broadened spectral features, the Doppler shift may become an important consideration for high-resolution spectroscopy.

Box & Whiskers—A Method to Reduce Periodic Noise

Light from a diode laser (distributed feedback or external cavity) is focused onto an acousto optics modulator (AOM). The first order diffraction beam from the AOM is steered into an optical cavity using "mode matching" optics. The cavity length is modulated over one or more free spectral range of the cavity using piezo actuator(s). Light exiting the cavity is detected. Upon detection of "resonance: in the cavity (detector voltage over a threshold), the AOM is de-energized, thus stopping the flow of light into the cavity. The detector voltage decays exponentially with a decay constant that is a function of the physical parameters of the cavity (mirror losses and length) and spectral properties of molecules that may be in the ring down cell. Several ring down events are collected at each wavelength. Statistical analysis of the ensemble of ring down events using a variable width "box and whiskers" sort improves precision. An entire spectrum may be collected by scanning the wavelength. In this case, concentrations are determined by fitting the spectrum to a simulate spectrum. To speed data acquisition, a "sensor" mode has also been used. Here spectral baseline points are collected on either side of the analytical feature of interest and three spectral data pts are collected near the features peak. These latter three points are fit to a parabola to locate the absolute peak maximum. The average of the baseline points determine the empty cavity decay constant. This data is correlated to the equivalent Voigt lien shape signal level to determine concentration. Finally, a correction signal is applied to the laser current to recenter the peak with respect to laser frequency. (due to drift).

Cluster Analysis

Another method involves Cluster Analysis. A series of ringdowns is fit and a 2 dimensional Agglomerate clustering algorithm is used, as shown in FIG. 16. Plotted below are decay constant (÷$10^4$) in units of sec−1 and fit quality (correlation coefficient. A number between 0 and 1 that indicates how good the fit is.) For this data, there is a dominant mode that produces good fits and a fairly consistent decay constant. Clustering allows us to sort this data into common groupings. The circles indicates a possible groupings (base don the statistics). This is implemented in real time. It is a way to compensate for misalignments and multimode cavity excitation. It is even better than the box and whiskers in that it does not assume a (normal) distribution around the population median.

Near-Infrared and Mid-Infrared Lasers

Near-IR lasers range from about 1 to about 2.5 micrometers and are well suited for detection of smaller trace species such as HCHO, H2S, METHYL MERCAPTAN, CO2, CO, HCN, HCl, NH3, and C2H2.

In another preferred embodiment described herein, the mid-IR OPO laser uses a periodically poled lithium niobate (PPLN) crystal. This system provides better sensitivity, less interference, and can detect a broader range of molecules due to its higher power, e.g. 100-500 mWatts.

Experimental Setup

Figure 1:
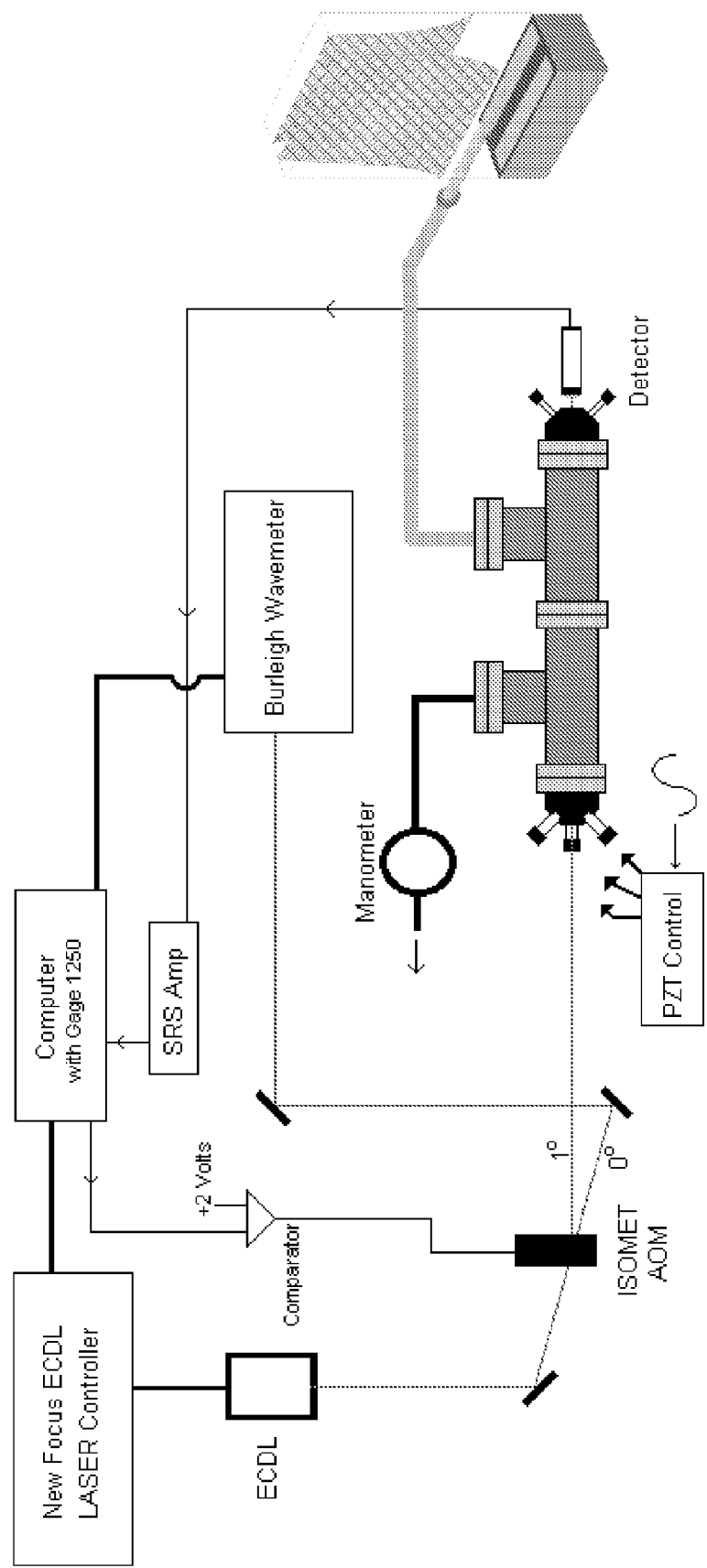
FIG. 1. Schematic layout of one of the preferred embodiments of an experimental setup.

The schematic layout of this cw-CRDS experiment is shown in FIG. 1. The light source used is an external cavity diode laser (ECDL) manufactured by New Focus (Velocity 6328). The ECDL has a continuous wavelength range from 1510-1580 nm with a maximum power of 8 mW (typical 6 mW) and a bandwidth of 5 MHz. Tuning the laser is accomplished by changing the angle between the tuning mirror and the grating (in the laser housing). A DC motor is used to course tune, while a piezo transducer (PZT) attached to the mirror is used to fine-tune the laser. A Burleigh wavemeter (WA-1000) determines the wavelength of light emitted by the laser throughout the scan.

A Gateway computer equipped with a Gage Compuscope 1250 PCI card was used to control the ECDL PZT voltage and fine tune the laser. The cavity length was modulated with the saw tooth function from a Stanford Research Systems function generator (SRS345) driving a Thor Labs piezo driver (MDT691). The driver output was fed to three identical PZTs symmetrically surrounding the mirror to scan the ringdown cavity length. An InGaAs pin detector in a Los Gatos Research CRDS package was placed after the second mirror. This detector was coupled with a current follower circuit to amplify the signal. When buildup occurred sufficiently to trigger the Gage card, the computer sent a three-volt signal to a comparator circuit that de-energizes the ISOMET Acousto-Optic Modulator (thus shutting off the light into the cavity). The Gage card then captured the ringdown and stored it to a file. For each step in the spectrum 100-200 ringdowns were captured on the Gage card and saved to the computer. Each ringdown was then fit to a single exponential decay to determine the decay constant. After data processing, the average decay was plotted versus wavelength to obtain a spectrum.

Mirrors with maximum reflectivity near 1.55 µm were obtained from Los Gatos Research and were used for the ringdown cavity. Over the range of wavelengths explored in this research, a slight wavelength dependence of reflectivity ($\Re$) was observed as indicated by variation in empty cavity decay constants (typical values of 15 µs at 1540 nm and 12.5 µs at 1570 nm were obtained). From these decay constants, reflectivity can be calculated from $$\Re = 1 - \frac{L_{cavity}}{\tau \times c} \quad (2)$$

where $L_{cavity}$ is the spacing between the mirrors, τ is the ringdown time and c is the speed of light. The cavity length was 0.26 m resulting in calculated mirror reflectivities of 0.999940 and 0.999928 (1−$\Re$=60 ppm and 72 ppm) at 1540 nm and 1570 nm, respectively.

Although a three mirror triangular or four mirror rectangular cavity can be utilized, in one preferred embodiment our instrument has a unique four mirror "bow-tie" cavity configuration. A bow-tie configuration provides the following advantages. First, it allows for a more compact sensor. Second, it eliminates optical feedback to the laser source. Third, ring resonators are inherently more stable. Fourth, it provides for a simplified alignment. Fifth, it allows for a longer optical interaction length. Sixth, it allows for uniformity of mirror optics.

Accordingly, the cavity consists of a high finesse resonator using four mirrors (preferably piano-concave). As contemplated, the laser beam strikes all four mirrors, making two passes through the cavity, i.e., four passes for one round-trip. When using all piano-concave mirrors, all four mirrors can be identical and can, therefore, be fabricated in a single coating run. The cost of a mirror coating run is high, so this simplification in mirror optics significantly reduces the CRDS system cost. As an alternative to four plano-concave mirrors, one can use two flat and two plano-concave mirrors. Again, although the mirror substrates would not all be identical, a single coating run could be carried out. In addition, if the input laser(s) do(es) not vary in frequency, only one of the mirrors of the cavity needs to be dithered to provide a resonant cavity.

For a desktop apparatus, the foot print of this prototype would be between about 6" to about 12" wide, preferrably 8.5" wide, by about 5" to about 8" deep, preferably 6.5" deep, by about 5" to about 8" tall, preferably 4" tall, as a bench-top device. In a preferred embodiment, the device weighs about 5 to about 12 pounds, and preferably weighing about 6 pounds. Further, it can be easily configured to fit in a 2U box for standard 19" rack.

Optimization of Experimental Variables and Data Analysis

Ideally, only one transverse mode of the laser beam should be excited with the cw-CRDS technique. This ensures that the laser beam is sampling a single location on the mirror surface. Sampling different locations results in complicated, multi-exponential ringdowns due to the inhomogeneous reflectivities of the surface of the mirror. A single transverse mode structure allows for the buildup of light in the cavity when the laser is an integer multiple of the cavity's FSR. Modulating the cavity length over one FSR results in a build-up event at any wavelength throughout the scan. As noted above, cavity length modulation is accomplished using three identical piezo-electric transducers (PZT) so as to prevent compromising the alignment.

Figure 2:
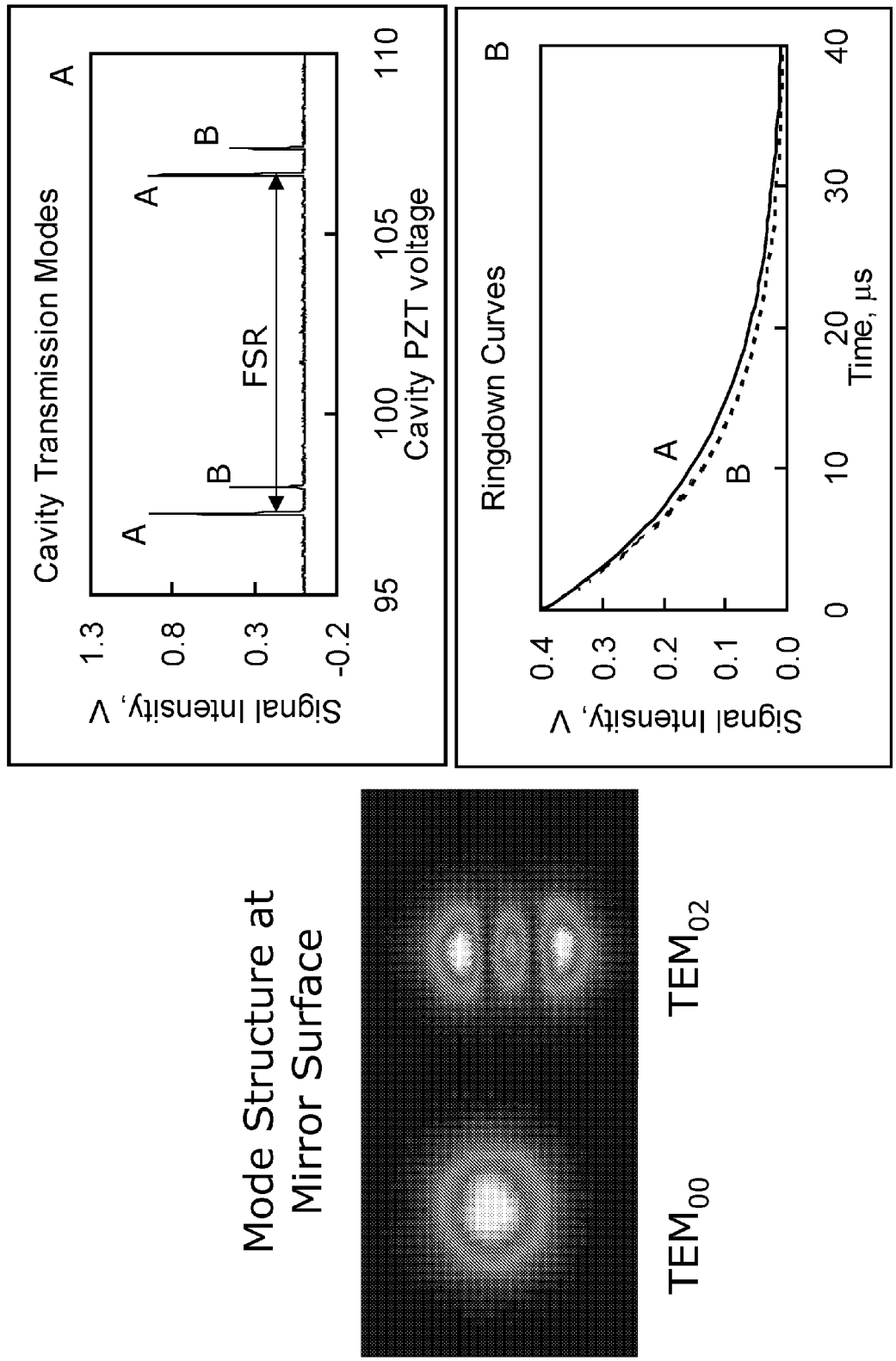
FIG. 2. The top graph shows two cavity transmission modes seen while modulating the cavity length. The goal here is the left side, which shows a single mode in an empty cavity. This can only result from a stable optic design and good algorithms. The resulting ringdowns for each transmission mode are shown in the bottom graph.

FIG. 2 shows the modulation of the cavity over a length corresponding to somewhat greater than one FSR. In this figure the cavity is slightly out of alignment to show two sets of two transverse cavity modes separated by one FSR. Further alignment of the cavity can select either of the transverse modes (labeled A and B). Ringdowns for the single mode operation were collected and are shown in FIG. 2B. As the data show, the ringdown times for peaks A and B are distinctly different (10.6 and 9.4 µs, respectively).

Figure 3:
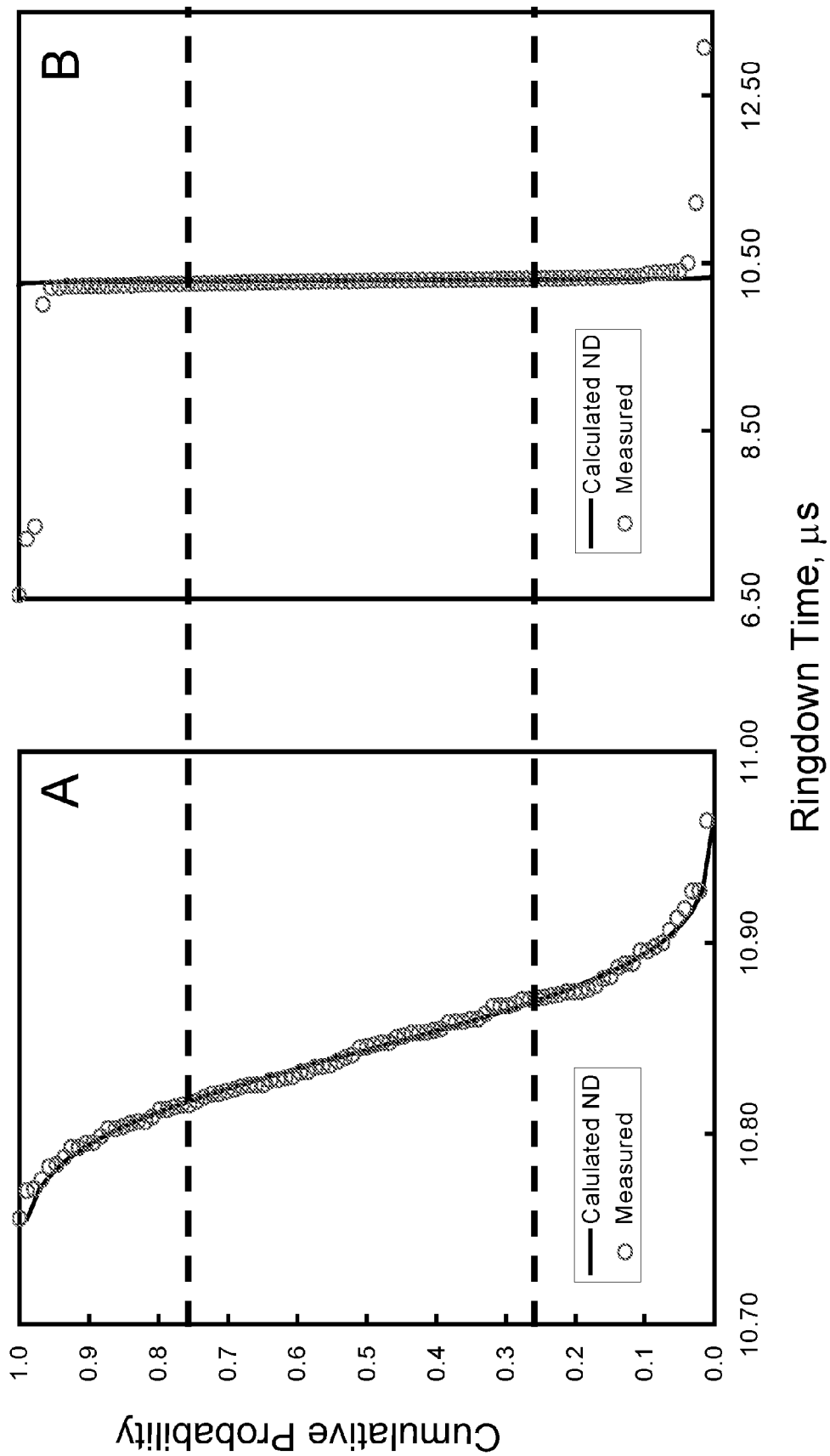
FIG. 3. A typical ringdown distribution acquired while taking a spectrum of $CO_2$. A normal distribution (ND) is calculated for each data set. A shows a data set that is normal, while B has decays that are well beyond the calculated normal values. The dashed line represents the interquartile range (IQR) of a box and whiskers analysis. The difference in the normalized standard deviation from A to B is reduced from $6.6 \times 10^{-2}$ to $1 \times 10^{-4}$ with the box and whiskers analysis.

Multi-mode excitation can be minimized through careful cavity alignment. However, when ramping the cavity length over several FSRs, any mismatch in the PZTs may lead to excitation of undesired modes. This applies to using three ganged drivers. Although the new annular piezos are free of this problem, statistical treatment of the data still helps. Fortunately, these extraneous points can be identified in analyzing the statistics of the individual ringdown events. As a figure of merit for evaluating the distributions of ringdown curves, we track the standard deviation normalized to the averaged ringdown time ($\sigma/\langle\tau\rangle$). FIG. 3A shows the distribution of 94 ringdowns captured while taking a spectrum of $CO_2$ in air which is well described by a normal distribution. Our figure of merit, $\sigma/\langle\tau\rangle$, for this data was $3.6\times10^{-3}$. FIG. 3B shows a ringdown distribution that contains several ringdowns in which undesired mode excitation occurred. For this set, $\sigma/\langle\tau\rangle$ was substantially greater, $6.8\times10^{-2}$. Romanini et al. also observed a "periodic noise" in their cw-CRD spectra when using cavity modulation. In their work, this periodic error is believed to be a result of a transmission mode excited near the end of the a cavity scan.

A "box and whiskers" analysis was employed to eliminate the outliers and reduce periodic noise. In this procedure, the decay constants are sorted and the upper and lower quartile values are discarded leaving the interquartile range (IQR), or middle fifty percent, to be averaged. The normalized standard deviation after a box and whiskers analysis ($\sigma/\langle\tau\rangle$ IQR) results in a significant improvement in the agreement between the two distributions: the averaged value of the IQR for FIG.

3A is 1.6×10−3 while that of FIG. 3B which is 1.7×10−3. It is contemplated herein that interquartile is not strictly limited to exactly the $25^{th}$-$75^{th}$ percentiles, and can vary as low as about the $20^{th}$ percentile and about the $80^{th}$ percentile, as well as combinations and permutations therebetween, e.g. 20-80, 20-75, 20-60, 25-75, 25-80, 25-60, 30-75, 30-60, 30-80, as would be known to persons of ordinary skill in this area.

Once a spectrum is obtained, it is fit with a simplex simulation routine to determine the mole fraction of the target species in the cell. The absorption coefficient (a) is calculated from $$\alpha_\lambda = \frac{\tau_{empty} - \tau_\lambda}{c \times \tau_{empty} \times \tau_\lambda} = S \times g \times \rho \times x_j \qquad (3)$$

where $\tau$ is ringdown time, c is the speed of light, S is linestrength, g is lineshape, $\rho$ is molecular density and x mole fraction of species j. The lineshape function in the fit can be Lorentzian, gaussian or Voigt depending on the pressure inside the cavity. In order to fit the data, all the spectroscopic constants such as self-broadening, air-broadening, temperature dependence, pressure shifts, line strengths and line positions are obtained from HITRAN 2000 for $H_2O$, CO and $CO_2$. The $NH_3$, $C_2H_2$ and HCN constants were obtained from the GIESA database or other publications and were optimized with the simplex fitting routine.

Results of cw-CRDS Spectra—Acetylene and Hydrogen Cyanide

For measurements of $C_2H_2$ and HCN, gas samples were extracted from a methane/air diffusion flame supported on a Wolfhard-Parker slot burner. This burner consist of an 8×41 mm fuel slot sandwiched between two 16×41 mm air slots. A quartz microprobe that ran parallel to the slot separators was used to sample the flame gases at 9 mm above the burner. At this flame height, two flame sheets are observed centered near 6.5 mm from the burner centerline. Both HCN and $C_2H_2$ concentrations were found to peak in the hydrocarbon pyrolysis region inside of the flame sheets, approximately 4 mm from the centerline.

Figure 4:
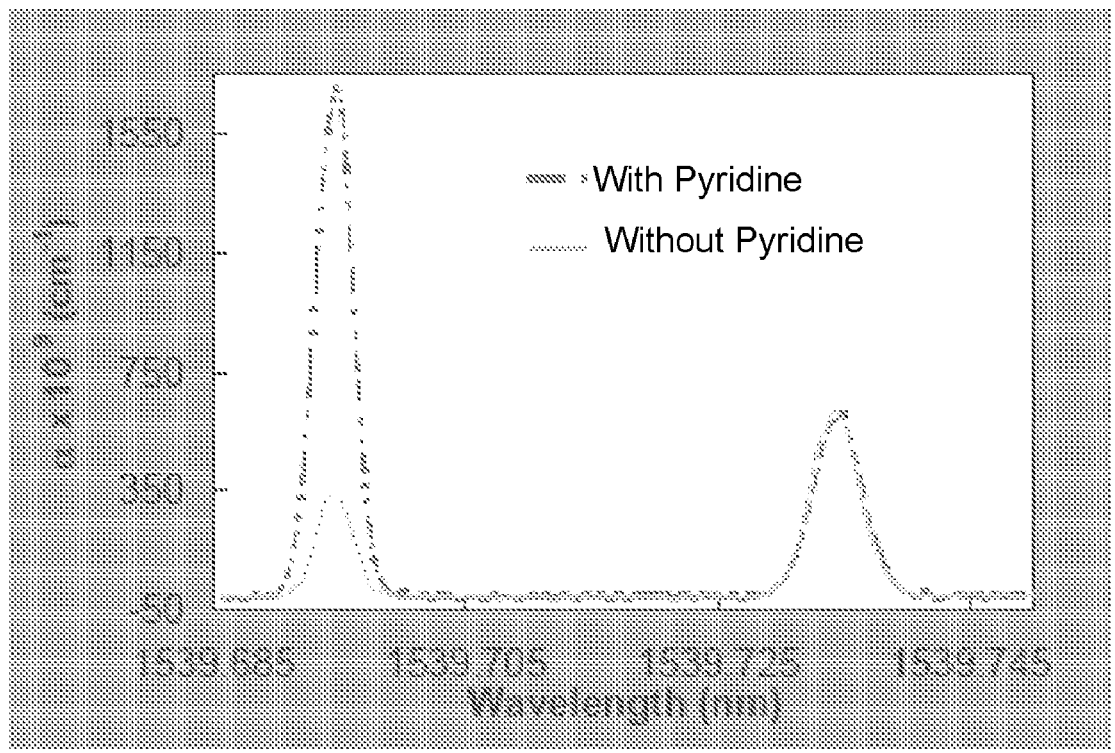
FIG. 4. Spectra obtained from a Wolfard-Parker burner at 9 mm HAB with and without the addition of pyridine to the fuel. the large peak to the left is HCN, the next peak is C2H2 (acetylene).

FIG. 4 shows a spectrum obtained in the flame near the peak in species concentrations. In order to identify the peaks a simulation of acetylene and hydrogen cyanide line positions was performed. The results were compared to the acetylene standard reference material data sheets from NIST to verify the accuracy of the simulation.

This confirmed the identity of a relatively weak acetylene absorption feature at 1539.735 nm. The GEISA database identified the peak at 1539.695 as HCN. As a simple experiment to verify this peak as HCN, the fuel was bubbled though pyridine, adding approximately 1% dopant to the fuel flow. Pyridine pyrolyzes to HCN quantitatively, resulting in a dramatic increase in peak intensity.

The values of $C_2H_2$ concentrations in the Wolfard-Parker burner have been reported using a mass spectrometric technique, which allows for the comparison with the calculated concentrations obtained with cw-CRDS. The agreement of these two values is within a percent suggesting the accuracy of our procedure.

Carbon Dioxide and Carbon Monoxide

To test the cw-CRD potential as a sensor for CO and $CO_2$, measurements were made of the pure gas at the strongest peaks available around 1570 nm that were free of interferences based on simulated spectra. The detection limits were then calculated by taking the standard deviation of the baseline to represent our noise level. A signal three times as high as the noise level resulted in detection limits of 2.0 ppm for CO and 2.5 ppm for $CO_2$. A detection limit on this order for $CO_2$ allows for its detection in ambient air, resulting in an easy measurement that requires no gas dilution.

FIG. 5 shows the accuracy of the fitting routine on a $CO_2$ line at 1572.33 nm (6360 $cm^{-1}$) in laboratory air. The line was fit with a Voigt lineshape for every pressure except 5 torr, for which a gaussian shape was assumed. The average calculated concentration from the fits was 453 ppm ($\sigma$=7.3 ppm).

Figure 6:
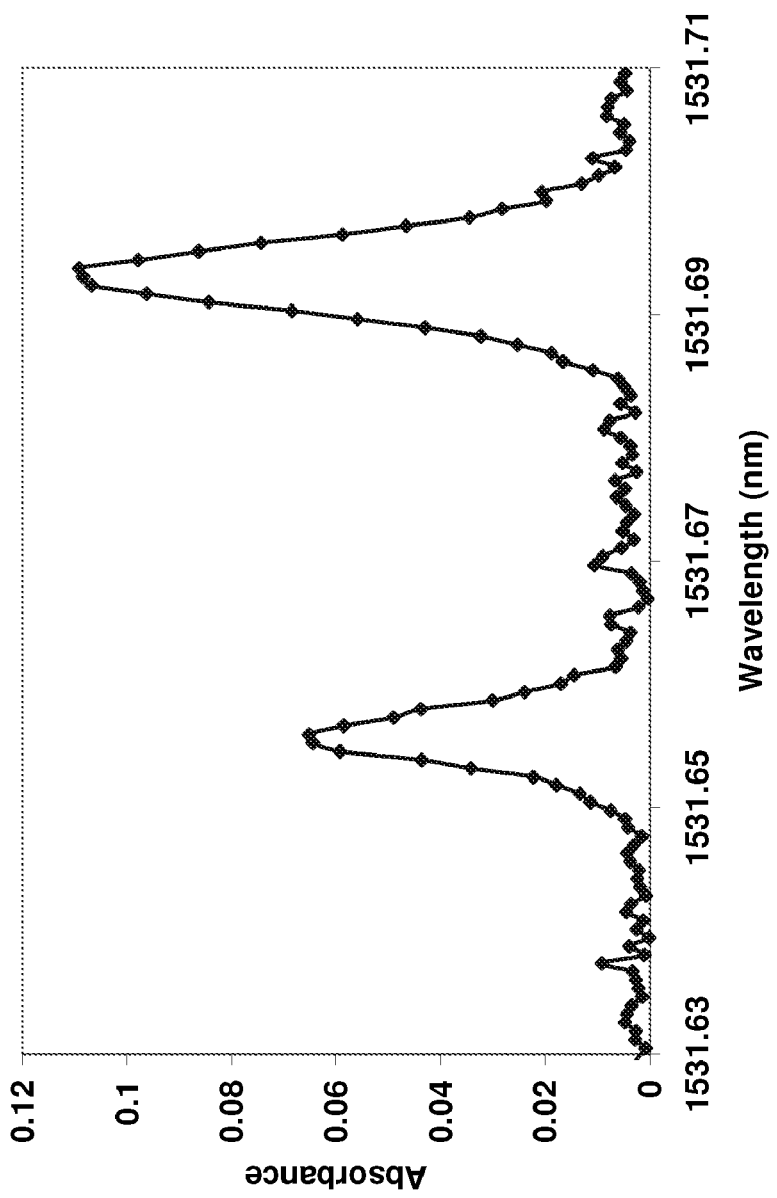
FIG. 6. A spectrum obtained with 50 torr laboratory air in the cavity with residual $NH_3$.

Ammonia $NH_3$ was injected into the empty cavity and then diluted with nitrogen gas. The dilution was sufficient to take the concentration below ppm levels in the cavity but due to the residual effects of $NH_3$ the resulting peak had a fit concentration well over 10 ppm. Without some other method of measuring $NH_3$ in the cavity we are unable to produce an accurate calibration curve. In an attempt to determine detection limits, acetylene was substituted for $NH_3$ since it has comparable linestrengths in this region. The $C_2H_2$ P4 line at 1527.44 was chosen because its calculated linestrength of 2.37×$10^{-21}$ $cm^{-1}$/(molecule·$cm^{-2}$) closely approximates the largest $NH_3$ line which has a reported value of 2.33×$10^{-21}$ $cm^{-1}$/(molecule·$cm^{-2}$). The calibration curve for this $C_2H_2$ line with the cw-CRDS setup resulted in a linear slope ranging from 53 ppm to 5 ppm. With the calibration of $C_2H_2$ it was possible to determine the residual concentration of $NH_3$ detected when ambient air was sampled. FIG. 6 shows a CRDS spectrum of air at 50 torr where the $NH_3$ peaks are clearly visible. The peak maximum absorbance of $NH_3$ corresponds to a concentration of 37 ppm.

Discussion of Results

When comparing the results from cw-CRDS to other absorption techniques it is useful to relate detection limits in terms of the absorption coefficient. It has been reported that CRDS can produce detection limits down to $10^{-10}$ $cm^{-1}$ with suitable mirrors. With the current experimental setup and mirrors, absorption coefficients of 3×$10^{-9}$ $cm^{-1}$ have been achieved (3$\sigma$ level). For other absorption techniques, where an increase in pathlength increases sensitivity, there must be a normalization of the absorption coefficient to compare it with CRD values. Direct, 2f—wavelength modulation, and high frequency modulation absorption techniques have absorbance detection limits[1] on the order of 1×$10^{-4}$, 5×$10^{-6}$ and 1×$10^{-6}$ respectively. To achieve comparable absorption coefficient sensitivities as those attainable using CRDS (3×$10^{-10}$), the pathlengths for these methods would need to be 3,333 meters for direct absorption, 167 meters for 2f modulation, and 33 meters for high frequency modulation.

Table 1 shows the calculated detection limits (3$\sigma$ level) for our sensor and for the molecules discussed above [1].

| Molecules | cw-CRDS DL |
| --- | --- |
| HCN | 7.9 ppb |
| CO | 2.0 ppm |
| $CO_2$ | 2.5 ppm |
| $NH_3$ | 19.4 ppb |
| $H_2O$ | 1.8 ppm |
| $C_2H_2$ | 4.0 ppb |

This cw-CRD system achieves sensitivities comparable to the best frequency modulation techniques requiring at least a 3-meter pathlength cell.

Analog Electronics

In another preferred embodiment an analog circuit replaces some of the control functions that used to be performed by external instrumentation. Analog allows for a smaller cavity and eliminates some of the hardware and electronics required otherwise. As such, an analog system may trade sensitivity for cost or other factors, where sensitivity at certain limits is not required. In this embodiment, voltage is generated on the board that tunes the laser through an external laser diode current source and a voltage ramp is generated on the board to drive the cavity length ramp (through an external piezo driver). The ramp is halted upon resonance n the hope that after a ring down event is recorded, the cavity will still be in resonance when the laser light is switched back on. In other words, bursts of events can be recorded. Although full digitization of the cavity decay curve may be used to determine the decay constant, here, a two point sample and hold circuit is used to determine the decay constant. A circuit board that implements these functions has been designed and breadboarded, including the use of a Basic Stamp microcontroller. Having the full ring down curve (and their exponential fits) allows not only a statistical advantage (several hundred data points determine each decay constant), but also allow the detection of "fault modes": multiexpoential decays, ineffective shuttering, etc. Although this can be implemented using a sophisticated digitizing card mounted in a PC, it can also utilize a Megasample per second embedded Analog to digital microcontrollers to do the job.

An analog detection scheme is used to measure the decay constant of the ring-down signals, requiring only a single voltage to be digitized and stored per ring-down. Curve fitting routines common to traditional digital methods are eliminated, allowing for measurement speeds limited only by the finite build up and decay time of light within the cavity. Near infrared spectra of ammonia and acetylene were obtained with this spectrometer with an extinction coefficient detection limit of $2\times10^{-8}$ cm$^{-1}$, equivalent to 180 ppbV for ammonia and 500 ppbV for acetylene for the specific lines investigated, at a pressure of 50 Torr. A comparison is made between ring-down data taken with this scheme and with a digital data acquisition card. From this comparison, the dominant source of noise appears to be non-exponential decay due to beating between multiple transverse modes.

Experimental Procedure

In this preferred embodiment, both the ring-down measurement and the cavity modulation strategy have been implemented with a custom built electronic circuit. A microcontroller is used for data processing, control of the laser frequency, and to send data to an external computer. A schematic of the electronics is shown in FIG. 9.

Spectra were acquired out using an external cavity diode laser (ECDL) operating at a wavelength of 1.53 μm (New Focus model 6328). The ECDL employs a Littman type laser cavity in which frequency changes are made by moving a tuning mirror. A piezoelectric transducer mounted on the back of the tuning mirror is used for fine frequency adjustments, and modulation of this transducer is limited to 2 kHz. The observed decay times are on the order of 15 μs. Thus, frequency detuning as a shuttering mechanism was not possible due to the slow response time of the external cavity. Therefore, an AOM is used to interrupt the beam when resonance is reached to allow for the decay of light in the cavity.

AOM

The AOM used in the experiments (Isomet Corporation model 1205-C1) has a switching time of tens of nanoseconds, providing a sufficiently sharp cutoff of the beam for ring-downs lasting several microseconds. When the AOM is energized, a fraction of the incident light is diffracted into the first order beam through an angle of 34 mrad with respect to the zeroth order beam. The first order beam is used to excite the cavity, and is turned off by de-energizing the AOM.

Layout

The experimental layout is shown in FIG. 10. A linear ring-down cavity is formed between a pair of 2 cm diameter mirrors of 99.99% reflectivity, spaced 0.5 m apart. Each mirror has a concave surface, with a 6 m radius of curvature. This forms a stable optical resonator with a free spectral range of 300 MHz. The mirrors are sealed with O-rings against 34 mm CF flanges, which are in turn welded to either end of a 1.9 cm (0.75") diameter stainless steel tube. The tube forms a gas sample cell, and is provided with three ports for gas inlet, exhaust, and a pressure tap. The mirror mounts are custom made assemblies designed to mate with the CF flanges. A schematic of the experimental arrangement and a detail of the mirror mounts are shown in FIG. 4 Analog.

Longitudinal modes of the cavity are matched to the laser frequency using an annular piezo-electric transducer (Physik Instrumente model P-0016.00H) to modulate the length of the cavity by a few free spectral ranges. This guarantees that an arbitrary laser frequency will match a cavity mode at some point during the modulation cycle. The transducer is mounted directly behind one cavity mirror, with the input beam passing through the hole in its center. The O-ring on the other side of the mirror provides the necessary compression to hold the mirror against the PZT, seals the mirror against the cavity, and allows for the small amount of movement required to modulate the cavity length.

"Sweep & Hold"—Cavity Modulation

In order to increase the measurement speed, coupling of light into the cavity is enhanced by a 'sweep and hold' cavity modulation technique. Matching of the cavity length to the laser frequency is accomplished by moving one of the cavity mirrors with a piezoelectric transducer. Resonance is detected by observing the build up of light in the cavity. When the intensity reaches a preset threshold, the AOM is switched off to interrupt light into the cavity and the PZT scan is paused. After the decay of light is recorded, the AOM is switched on. If the laser frequency and cavity mode are still resonant, light again builds up in the cavity. This process is repeated as long as resonance is maintained. If light fails to build up in the cavity after a few hundred microseconds, scanning of the mirror is resumed. This process is shown pictorially in FIG. 8. Rather than a single ring down each time the cavity is brought into resonance, a burst of ring downs is generated. This burst lasts until resonance is lost due to drift in the laser or mechanical and thermal instabilities in the cavity. During the resonance period, ring-downs may be generated at a rate limited only by the finite build up and decay time of the cavity itself, on the order of tens of kilohertz. In preferred embodiments, about 1 to about 10 kHz, and more preferably about 10 to about 20 kHz.

In experiments, each burst of ring-downs typically lasts for no more than 5-10 ms, although on occasion they may last for several hundred milliseconds. It should be noted that although we were able to generate ring-downs at ten kilohertz, the speed of the random access memory used by our microcontroller limited the recording of decay times to a rate of only 1 kHz. The sweep and hold method has the added advantage of holding the cavity length constant during each ring down, as opposed to the continuous sweep method. This eliminates the problems caused by a moving cavity mirror, and thus an arbitrary modulation frequency may be used without compromising the resolution or accuracy of the spectrometer.

Alignment of the cavity is performed manually with three adjustment screws on each mirror mount. Mode matching optics and a spatial filter are used to match the input beam to the TEM$_{00}$ mode of the cavity, although there was still some difficulty in suppressing multimode excitation. It should be noted that we could not directly determine whether the TEM$_{00}$ mode is in fact the dominant mode in the cavity. There are usually several transverse modes that are excited over one free spectral range, even with careful alignment. A threshold level is adjusted to ensure that only ring-downs from the dominant mode are measured.

Analog Time Constant Measurement

Light transmitted by the cavity is detected with an InGaAs photodiode (Thorlabs model FGA10). The signal from this photodiode is amplified with a transimpedance amplifier having a gain of 1 V/μA. Ring-down measurements begin when the detector signal exceeds a preset threshold level. This causes a trigger signal to de-energize the AOM, interrupting the input beam. The decay of light remaining in the cavity is then measured with an analog circuit using a two-point measurement based on the voltage level of the signal. The measurement is made with a linear voltage ramp produced as the signal falls between two reference voltages, as illustrated in FIG. 7. The final voltage reached by the ramp is proportional to the decay time. The second reference voltage is fixed at one third of the first, so the measurement takes place over ln(3)= 1.1 time constants. Note that the measurement always takes place in the same fraction of a time constant. This allows optimal accuracy to be maintained over a broad range of decay times. The final voltage reached by the ramp is directly proportional to decay time and thus requires only a single value to be digitized and stored per ring down. This increases the maximum rate at which data can be taken and greatly reduces data processing requirements when compared to digital methods.

Results

Spectra of ammonia and acetylene at several ppmv concentration in air were obtained to test the measurement and control procedure. The low concentrations were achieved by successive dilutions with room air. Laser frequency calibration was done with a wavemeter (Burleigh Instruments model WA-1000).

It was found that the decay time of the cavity exhibits sinusoidal oscillations with wavelength. The amplitude of oscillation is 1.8 μs, and the period is 0.118 nm. This period corresponds to that of an etalon with the same thickness as the mirrors used in the cavity, and is most likely due to the finite reflectivity of the back surfaces of the mirrors. This causes the mirrors to behave as etalons as the laser wavelength is scanned through their free spectral range. The oscillations are illustrated in FIG. 11. A baseline scan was taken with room air, and the result is shown in the figure with a sinusoidal fit. Because they are attributed to mirror behavior and do not represent absorption, these oscillations have been fit to a sinusoidal baseline decay time in the analysis of spectral data.

Examples of ammonia and acetylene spectra are shown in FIG. 12, taken using the experimental setup shown in FIG. 7. These spectra were taken at room temperature and 50 Torr cavity pressure. This pressure is chosen as a compromise between minimizing pressure broadening and maximizing peak absorbance. One hundred ring-downs were taken at each spectral point and averaged. The best detection limit achieved with this system is $2 \times 10^{-8}$ cm$^{-1}$ with 100 ring-down averaging, based on a signal to noise ratio of 3.

Also shown in FIG. 12 are spectral fits to the data. For ammonia, these spectral fits were generated using a Voight profile with line strength data taken from Webber et al. The ammonia lines are among those recommended by Webber et al for air quality monitoring within the $2\nu_3$ overtone and ($\nu_1+\nu_3$) combination bands: the $^PP_3(5)_a$ line at 6528.764 cm$^{-1}$, and an unassigned line at 6528.894 cm$^{-1}$. The line strengths are $2.53 \times 10^{-21}$ cm$^3$/(molecule×cm$^2$) and $1.34 \times 10^{-21}$ cm$^3$/(molecule×cm$^2$), respectively. The line assignment is taken from Lundsberg-Nielsen et al. Acetylene has several vibrational bands in the near infrared spectral region that are either $\Sigma\Sigma \neg \Sigma\Sigma$ or $\Pi\Pi \neg \Sigma\Sigma$. The strongest lines are combinations of strong C—H stretching modes. A NIST frequency standard using acetylene capitalizes on the regular progression of the $1010^00^0 \neg 0000^00^0$ ($\nu_1+\nu_3$) combination band. In addition, several hot bands exist in which the lower states have populations in low frequency bending modes leading to several weaker transitions evident in the high-resolution spectrum between the larger features of the ground state transitions. Line strengths for these features can be determined by fitting the high-resolution spectrum of the NIST SRM to a Voight line shape using the conditions of this gas sample. For the features shown in FIG. 12, these lines are 6494.51 cm$^{-1}$ and 6494.62 cm$^{-1}$, with line strengths of $4.70 \times 10^{-22}$ cm$^3$/(molecule×cm$^2$) and $1.83 \times 10^{-22}$ cm$^3$/(molecule×cm$^2$), respectively. Due to variability in the ECDL tuning between successive scans, there is up to 0.1 cm$^{-1}$ offset error in the frequency axis. This error has been removed using the published line positions for the selected ammonia and acetylene lines shown in FIG. 12.

Internal Comparison—Digital vs. Analog

In order to evaluate the performance of the two-point measurement scheme, ring-down measurements were compared with measurements made by a digital data acquisition system. The digital measurements were obtained using a high-speed digitizer (Gage Applied Technologies, Inc. model CS1250), and then fitting the data to a single exponential decay. The analog circuitry and the digitizer measured each ring-down simultaneously in order to provide a direct comparison of the two methods. The spread in the decay times acquired using each method is plotted in FIG. 13 for 200 ring-downs. The standard deviation in the data between the two methods is about the same, but the noise is not well correlated between them. If it were, all the data should fall on a straight line with a slope of unity. The fact that it does not is indicative of a deviation from the assumed exponential behavior of the ring down signal.

It was discovered upon examination of the digitally recorded signals that most of the ring-down events are not single exponential decays, but rather contain an oscillating component superimposed on an exponential decay. The amplitude of this oscillation varies between different ring-downs, and may account for the discrepancy in ring down values found from the two measurement methods. The residual between the recorded signal and an exponential fit for a representative ring-down is shown in FIG. 14. The period of the fluctuations is about half of one decay constant, corresponding to a time of 6 μs. Similar oscillations have also been noted by Romanini et al. and by Paldus et al. Romanini attributed this to beating between different transverse modes at slightly different frequencies, and we believe the same to be the case in our experiments.

Suppression of spurious transverse modes by proper mode matching is important in eliminating this source of noise. One limitation for mode matching with the current experimental setup is the use of an AOM to switch the beam on and off. The AOM has a wavelength dependent deflection angle, which for the first order diffracted beam is given by the expression $$\theta = \frac{\lambda f}{v_s},$$

where $\lambda$ is the laser wavelength, f is the acoustic frequency, and $v_s$ is the sound speed in the modulator crystal. The propagation angle of the input beam will change linearly with wavelength during the course of a spectral scan due to this effect, introducing a slight alignment error of the beam at the input mirror of the cavity. As pointed out by Wheeler et al., transverse mode beating effects can also be minimized by focusing the entire cross section of the output beam onto the detector.

Thus, a new method of cavity ring-down time constant measurement and mode matching technique has been provided. This allows for the lower data processing and power requirements with increased acquisition speeds useful for more compact and energy efficient ring-down spectrometers suitable for portable applications. In a portable device, the analog circuit is incorporated into the instrument design. For example, a stand-alone function generator would not be used to create ramps, but rather these are built in.

Detection limits for ammonia and acetylene for the spectral lines used in this investigation were 180 ppbV and 500 ppbV, respectively. In the case of acetylene, the measurement was based on relatively weak transitions in the $(v_1+v_3)$ combination band. Spectroscopy based on the strongest line in the $(v_1+v_3)$ band would allow for a reduction in measurable concentration to 17 ppbV at the same extinction coefficient.

A potential advantage of Approach One is that having the full ring down curve (and their exponential fits) allows not only a statistical advantage (several hundred data points determine each decay constant), but also allow the detection of "fault modes": multiexpoential decays, ineffective shuttering, etc.

FIG. 15 shows a detailed schematic of one preferred embodiment of a commercial implementation of the subject matter herein.

EXAMPLES

Example 1

A CRDS apparatus using near-IR as described is installed in an aircraft to monitor trace species relevant to fire detection. It would be expected that there would be a significant improvement in reducing the number of false alarms which cause mandatory grounding and inspection of aircraft and thus generate a significant savings in aircraft maintenance costs.

Example 2

A CRDS apparatus using near-IR as described is installed in a commercial office building, e.g. the HVAC system to monitor trace species relevant to fire detection. It would be expected that there would be a significant improvement in reducing the number of false alarms and in improving the sensitivity of such fire detection devices and thus generating a significant savings in building maintenance and safety costs.

Example 3

A CRDS apparatus using mid-IR as described is installed in an aircraft to monitor trace species relevant to air quality and safety, e.g. chemical weapons. It would be expected that there would be a significant improvement in improving the detection of large molecule toxins as well as in reducing the number of false alarms which cause mandatory grounding and inspection of aircraft and thus generate a significant savings in aircraft maintenance costs.

Example 4

A CRDS apparatus using mid-IR as described is installed in a commercial office building, e.g. the HVAC system to monitor trace species relevant to air quality and public safety, e.g. chemical weapons. It would be expected that there would be a significant improvement in improving the detection of large molecule toxins as well as reducing the number of false alarms of such air sample detection devices and thus generating a significant savings in building maintenance and safety costs.

Example 5

A CRDS apparatus using either mid-IR or near-IR as described is installed in a public transportation system or vehicle to monitor trace species relevant to fire detection. It would be expected that there would be a significant improvement in reducing the number of false alarms and in improving the sensitivity of such fire detection devices and thus generating a significant savings in transportation maintenance and safety costs.

Example 6

A CRDS apparatus using either mid-IR or near-IR as described herein is installed in a public transportation system or vehicle to monitor trace species relevant to air quality and safety, e.g. chemical weapons. It would be expected that there would be a significant improvement in improving the detection of large molecule toxins as well as in reducing the number of false alarms which cause mandatory shut-down and inspection of transportation systems and thus generate a significant savings in maintenance costs.

Example 7

A CRDS system as shown in FIG. 15. Specifically, A compact cavity ring down spectroscopy system for detection and measurement of trace species in a sample gas, which comprises: i) a housing for said system; ii) an optics subsystem within said housing; and iii) an electronics and software subsystem within said housing and in electronic communication with said optics subsystem; wherein said optics subsystem, comprises: a tunable low-power solid-state continuous wave diode laser mounted on a current and temperature controlled board, said laser selected from the group consisting of a near-infrared diode laser and a mid-infrared diode laser; an acousto-optic modulator in fiberoptic communication with said laser for steering a first order diffraction beam of said laser and for interrupting said beam when resonance is achieved; a ring down resonant cavity for holding a sample gas, said cavity constructed of a machined monolithic metal block, said metal selected from the group consisting of aluminum and invar, said cavity cell receiving said first order diffraction beam of said laser and comprising at least four high-reflectivity mirrors, wherein said mirrors define an intracavity light path and one of said mirrors is a movable tuning mirror; a sample gas in-port operably connected to said cavity cell for introducing a sample gas into the cavity cell and a sample gas out-port operably connected to said cavity cell for expelling sample gas from the cavity cell; a piezo transducer drive attached to the tuning mirror for modulating cavity length to maintain resonance between the laser frequency and cavity modes, said piezo transducer drive operably connected to a piezo electronics driver circuit having a range of from about 100 volts to about 1000 volts, and said piezo electronics driver circuit controlled by a piezo transducer control having a range from about 10 volts to about 100 volts; a photo-detector for receiving said beam from the cavity and for generating a resonance signal and a voltage decay (ring down) signal, thereby measuring an interaction of said sample with said intracavity beam; and an amplifier for receiving and amplifying said resonance signal and said voltage decay (ring down) signal; and, wherein said electronics and software subsystem, comprises: a cell pressure electronic control unit; a pump flow unit control unit controlled by the cell pressure electronic control unit, said pump flow control unit operably connected to the sample gas in-port and the sample gas out-port of the optics subsystem; an analog electronic unit in electronic communication with one or more control units of the system including control units for the current and temperature control board, AOM, piezo electronics, detector, amplifier, cell pressure, and pump control; and a programmable microcontroller connected to the analog electronic unit, said microcontroller having upgradable electronic tuning and having a generic analog or digital communication protocol with a computer, e.g. an RS232 connection and the like attached thereto for communication with an external computer. The system may optionally further comprise software for reducing the periodic noise in the voltage decay signal by recording the cw-CRD voltage decay signals as data and subjecting the data to an algorithm selected from a cluster analysis or an averaging of the interquartile range of the data.

Example 8

An optics subsystem, as a separate unit, for use in a compact cavity ring down spectroscopy system for the detection and measurement of trace species in a sample gas, is also contemplated as one of the preferred embodiments of the present inventive subject matter. Said subsystem comprising: a tunable low-power solid-state continuous wave diode laser mounted on a current and temperature controlled board, said laser selected from the group consisting of a near-infrared diode laser and a mid-infrared diode laser; an acousto-optic modulator in fiberoptic communication with said laser for steering a first order diffraction beam of said laser and for interrupting said beam when resonance is achieved; a ring down resonant cavity for holding a sample gas, said cavity constructed of a machined monolithic metal block, said metal selected from the group consisting of aluminum and invar, said cavity cell receiving said first order diffraction beam of said laser and comprising at least four high-reflectivity mirrors, wherein said mirrors define an intracavity light path and one of said mirrors is a movable tuning mirror; a sample gas in-port operably connected to said cavity cell for introducing a sample gas into the cavity cell and a sample gas out-port operably connected to said cavity cell for expelling sample gas from the cavity cell; a piezo transducer drive attached to the tuning mirror for modulating cavity length to maintain resonance between the laser frequency and cavity modes, said piezo transducer drive operably connected to a piezo electronics driver circuit having a range of from about 100 volts to about 1000 volts, and said piezo electronics driver circuit controlled by a piezo transducer control having a range from about 10 volts to about 100 volts; a photo-detector for receiving said beam from the cavity and for generating a resonance signal and a voltage decay (ring down) signal, thereby measuring an interaction of said sample with said intracavity beam; and an amplifier for receiving and amplifying said resonance signal and said voltage decay (ring down) signal.

An electronics and software subsystem, as a separate unit, for use in a compact cavity ring down spectroscopy system for the detection and measurement of trace species in a sample gas, said subsystem comprising: a cell pressure electronic control unit; a pump flow unit control unit controlled by the cell pressure electronic control unit, said pump flow control unit operably connected to the sample gas in-port and the sample gas out-port of the optics subsystem; an analog electronic unit in electronic communication with one or more control units of the system including control units for the current and temperature control board, AOM, piezo electronics, detector, amplifier, cell pressure, and pump control; and a programmable microcontroller connected to the analog electronic unit, said microcontroller having upgradable electronic tuning and having an analog or digital connection attached thereto for communication with an external computer.

It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

I claim:

1. A compact cavity ring down spectroscopy apparatus for detection and measurement of trace species in a sample gas, which comprises: a housing for said apparatus;

a tunable low-power solid-state continuous wave near-infrared diode laser within said housing;

an acousto-optic modulator in fiber optical communication with said laser for steering a first order diffraction beam of said laser and for interrupting said beam when resonance is achieved;

a ring down resonant cavity within the housing for holding a sample gas, said cavity cell receiving said first order diffraction beam of said laser and comprising at least two high-reflectivity mirrors, wherein said mirrors define an intracavity light path and one of said mirrors is a movable tuning mirror;

a piezo transducer drive attached to the tuning mirror for modulating cavity length to maintain resonance between the laser frequency and cavity modes;

a photo-detector within said housing, for receiving said beam from the cavity and for generating a resonance signal and a voltage decay (ring down) signal, thereby measuring an interaction of said sample with said intracavity beam; and a microprocessor for reducing the periodic noise in the voltage decay signal by recording the cw-CRD voltage decay signals as data and subjecting the data to an algorithm selected from a cluster analysis or an averaging of the interquartile range of the data configured as a desktop apparatus wherein the foot print is between about 6" to about 12" wide, by about 5" to about 8" deep, by about 5" to about 8" tall.

2. The apparatus of claim 1, configured as a desktop apparatus wherein the foot print is between about 8.5" wide, by about 6.5" deep, by about 4" tall.

3. The apparatus of claim 1, configured to weigh about 5 pounds to about 12 pounds.

4. The apparatus of claim 1, configured to weigh about 6 pounds.

* * * * *